US011180608B2

(12) United States Patent
Fukushima et al.

(10) Patent No.: US 11,180,608 B2
(45) Date of Patent: *Nov. 23, 2021

(54) BIODEGRADABLE POLYMERS, COMPLEXES THEREOF FOR GENE THERAPEUTICS AND DRUG DELIVERY, AND METHODS RELATED THERETO

(71) Applicants: INTERNATIONAL BUSINESS MACHINES CORPORATION, Armonk, NY (US); AGENCY FOR SCIENCE, TECHNOLOGY AND RESEARCH, Singapore (SG)

(72) Inventors: Kazuki Fukushima, Yamagata (JP); James L. Hedrick, Pleasanton, CA (US); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 507 days.

This patent is subject to a terminal disclaimer.

(21) Appl. No.: 15/397,193

(22) Filed: Jan. 3, 2017

(65) Prior Publication Data

US 2017/0114182 A1 Apr. 27, 2017

Related U.S. Application Data

(62) Division of application No. 12/645,931, filed on Dec. 23, 2009, now abandoned.

(51) Int. Cl.
| | |
|---|---|
| *A61K 47/34* | (2017.01) |
| *C12N 15/88* | (2006.01) |
| *C08G 63/64* | (2006.01) |
| *C08G 63/91* | (2006.01) |
| *C08G 64/02* | (2006.01) |
| *C08G 64/42* | (2006.01) |
| *C08G 63/06* | (2006.01) |
| *C08G 64/38* | (2006.01) |
| *C12N 5/00* | (2006.01) |
| *C08G 64/18* | (2006.01) |
| *C08G 64/30* | (2006.01) |

(52) U.S. Cl.
CPC .............. *C08G 63/64* (2013.01); *A61K 47/34* (2013.01); *C08G 63/06* (2013.01); *C08G 63/912* (2013.01); *C08G 64/0208* (2013.01); *C08G 64/0241* (2013.01); *C08G 64/18* (2013.01); *C08G 64/30* (2013.01); *C08G 64/38* (2013.01); *C08G 64/42* (2013.01); *C12N 5/0068* (2013.01); *C12N 15/88* (2013.01); *C08G 2261/126* (2013.01); *C12N 2533/30* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 3,223,678 | A | 12/1965 | Bolgiano |
| 4,443,593 | A | 4/1984 | Collins |
| 5,466,877 | A | 11/1995 | Moore |
| 6,521,736 | B2 | 2/2003 | Watterson et al. |
| 6,699,724 | B1 | 3/2004 | West et al. |
| 8,361,495 | B2 | 1/2013 | Hedrick et al. |
| 8,470,891 | B2 | 6/2013 | Hedrick et al. |
| 2008/0281044 | A1 | 11/2008 | Monahan et al. |
| 2009/0208553 | A1 | 8/2009 | Kemp et al. |
| 2009/0247666 | A1 | 10/2009 | Yu et al. |
| 2010/0015433 | A1 | 1/2010 | Arfsten et al. |
| 2011/0150977 | A1 | 6/2011 | Hedrick et al. |
| 2011/0151566 | A1 | 6/2011 | Hedrick et al. |
| 2011/0152167 | A1 | 6/2011 | Hedrick et al. |

FOREIGN PATENT DOCUMENTS

| | | |
|---|---|---|
| JP | 2000026582 A | 1/2000 |
| JP | 2001253940 A | 9/2001 |
| JP | 2007538097 A | 12/2007 |
| JP | 2009030051 A | 2/2009 |
| JP | 2009537660 A | 10/2009 |
| WO | 2009100645 A1 | 8/2009 |

OTHER PUBLICATIONS

Tyson et al., Biomacromolecules, online Dec. 8, 2008, 10: 149-154.*
Nifant'ev et al., Russian Journal of Organic Chemistry, 2005, 41: 1116-1121.*
Trolssas et al., Macromolecules, 1997, 30: 8508-8511.*
Zhang et al., J. Control. Rel., 2006, e28-e29.*
Niidome et al. , Gene Therapy, 2002,9: 1647-1652.*
Wen et al., Bioconjug. Chem., 2009, 20: 322-332.*
Corsi et al., Biomaterials, 2003, 24: 1255-1264.*
Ilies, Eur. J. Org. Chem., 2003, 14: 2645-2655.*
Martin, Curr. Pharm. Design, 2005, 11: 375-394.*
Zhang, J. Controlled Rel., 2004: 165-180.*
Almofti, Archiv. Biochem. Biophys, 2003, 410: 246-253.*
Thanou, Biomaterials, 2002, 23: 153-159.*

(Continued)

*Primary Examiner* — Ileana Popa

(74) *Attorney, Agent, or Firm* — Michael R. Roberts

(57) ABSTRACT

A biodegradable cationic polymer is disclosed, comprising first repeat units derived from a first cyclic carbonyl monomer by ring-opening polymerization, wherein more than 0% of the first repeat units comprise a side chain moiety comprising a quaternary amine group; a subunit derived from a monomeric diol initiator for the ring-opening polymerization; and an optional endcap group. The biodegradable cationic polymers have low cytotoxicity and form complexes with biologically active materials useful in gene therapeutics and drug delivery.

25 Claims, 5 Drawing Sheets

(56) References Cited

OTHER PUBLICATIONS

Biela, et al., "One-Pot Synthesis of Star-Shaped Aliphatic Polyesters with Hyperbranched Cores and Their Characterization with Size Exclusion Chromatography," J.Polymer Science PartA Polymer Chemistry, vol. 44, 4214-4221 (2006).
Bourissou, et al., "Recent advances in the controlled preparation of poly(a-hydroxy acids): Metal-free catalysts and new monomers," Comptes Rendus Chimie, vol. 10 (2007), 775-794.
Coulembier, et al., "From controlled ring-opening polymerization to biodegradable aliphatic polyester: Especially poly(b-malic acid) derivatives," Prog. Polym. Sci., vol. 31 (2006), 723-747.
De Villiers, et al., Nanotechnology in Drug Delivery, Biotechnology: Pharmaceutical Aspects, V 10, of Biotechnology (Arlington, VA.) Chap. 12, pp. 385-422.
Detrembleur, et al., "New Functional Aliphatic Polyesters by Chemical Modification of Copolymers of e-Caprolactone with gamma-(2-Bromo-2-methylpropionate)-e-caprolactone, gamma-Bromo-e-caprolactone, and a Mixture of β- and gamma-Ene-e-caprolactone," Macromolecules, 2000, 33 (21), pp. 7751-7760; published Sep. 29, 2000.
Dove, "Controlled ring-opening polymerisation of cyclic esters: polymer blocks in self-assembled nanostructures," Chem. Commun., 2008, 6446-6470.
EPO extended search report for PCTSG2010000487 dated May 7, 2013, EPO application No./patent No. 10839919.7-1302/2516504.
European Examination Report dated Oct. 21, 2013, Application 10 839 919.7-1302.
Gosselin, et al., "Efficient Gene Transfer Using Reversibly Cross-Linked Low Molecular Weight Polyethylenimine", Bioconjugate Chemistry, vol. 12, No. 6, Nov. 1, 2001, pp. 989-994.
Hu, et al., "Aliphatic Poly(ester-carbonate)s Bearing Amino Groups and Its RGD Peptide Grafting," Journal of Polymer Science: Part A: Polymer Chemistry, vol. 46, 7022-7032 (2008).
Jerome, et al., "Recent advances in the synthesis of aliphatic polyesters by ring-opening polymerization," Adv. Drug Delivery Reviews, vol. 60 (2008), 1056-1076.
Kamber, et al., "N-Heterocyclic Carbenes for the Organocatalytic Ring-Opening Polymerization of #-Caprolactone," Macromolecules, 2009, 42(5), 1634-1639).
Kamber, et al., "Organocatalytic Ring-Opening Polymerization", Chem. Rev., 2007, 107, 5813-5840.
Kamps, et al., "Urea-bearing copolymers for guest-dependent tunable self-assembly", J. Chem. Commun., 2007, pp. 954-956.
Kenawy et al., "The Chemistry and Applications of Antimicrobial Polymers: A State-of-the-Art Review" Biomacromolecules, vol. 8, No. 5, May 2007, pp. 1359-1384.
Kim, et al., "Mixed Micelle Formation through Stereocomplexation between Enantiomeric Poly(lactide) Block Copolymers", Macromolecules 2009, 42, pp. 25-29.
Lee, et al., "Quaternized Polyamidoamine Dendrimers as Novel Gene Delivery System: Relationship between Degree of Quaternization and Their Influences", Bull. Korean Chem. Soc. 2003, vol. 24, No. 11, pp. 1637-1640.
Liu, et al.."Ring-opening copolymerization of α-chloromethyl-α-methyl-βpropionolactone with ϵ-caprolactone," Macromolecular Rapid Communications, vol. 20, Issue 9, pp. 470-474, Sep. 1999; first published online Aug. 18, 1999.
Lv, et al., "Toxicity of cationic lipids and cationic polymers in gene delivery," Journal of Controlled Release 114 (2006) 100-109; Available online May 13, 2006.
Mecerreyes, et al., "Ring-opening polymerization of 6-hydroxynon-8-enoic acid lactone: Novel biodegradable copolymers containing allyl pendent groups," Journal of Polymer Science Part A: Polymer Chemistry, vol. 38, Issue 5, pp. 870-875, Mar. 1, 2000; first published online: Feb. 8, 2000.
Mei, et al., "Synthesis and Characterization of Novel Glycerol-Derived Polycarbonates with Pendant Hydroxyl Groups", Macromol. Rapid Commun. 2006, 27, 1894-1899.
Mindemark, J., Dissertation, "Functional Cyclic Carbonate Monomers and Polycarbonates, Synthesis and Biomaterials Applications" Uppsala Universitet, Sweden, copyright 2012 Jonas Mindemark, presented May 4, 2012, pp. 40-48.
Mintzer, et al., "Nonviral Vectors for Gene Delivery", Chem. Rev. 2009, 109, pp. 259-302.
Nederberg et al., "Organocatalytic Ring Opening Polymerization of Trimethylene Carbonate", Biomacromolecules, 2007, 8, 153-160.
Ochi, et al., "Phase Structure and Thermomechanical Properties of Primary and Tertiary Amine-Cured Epoxy/Silica Hybrids," Journal of Polymer Science: Part B: Polymer Physics, vol. 39, 1071-1084 (2001).
Palermo, et al., "Chemical Structure of Cationic Groups in Amphiphilic Polymethacrylates Modulates the Antimicrobial and Hemolytic Activities", J. Biomacromolecules 2009, 10, pp. 1416-1428.
PCT/SG2010/000487, filing date Dec. 23, 2010 International Search Report and Written Opinion.
Pospiech, et al., "Multiblock Copolymers of l-Lactide and Trimethylene Carbonate,"Biomacromolecules, 2005, 6 (1), pp. 439-446; Publication Date (Web): Dec. 17, 2004.
Pounder, et al., "Metal free thiol-maleimide 'Click' reaction as a mild functionalisation strategy for degradable polymers", Chem. Commun., 2008, 5158-5160.
Pratt, et al., "Tagging alcohols with cyclic carbonate: a versatile equivalent of (meth)acrylate for ring-opening polymerization", Chem. Commun., 2008, pp. 114-116.
Pratt, et al., "Tagging alcohols with cyclic carbonate: a versatile equivalent of (meth)acrylate for ring-opening polymerization", J. Chem. Commun., 2008, pp. 114-116.
Radowski, et al., "Supramolecular Aggregates of Dendritic Multishell Architectures as Universal Nanocarriers," Angew. Chem. Int. Ed. 2007, 46, 1265-1269.
Reineke, et al., "Structural Effects of Carbohydrate-Containing Polycations on Gene Delivery. 2. Charge Center Type," Bioconjugate Chem. 2003, 14, 255-261; Published on Web Dec. 21, 2002.
Reschel, et al., "Physical properties and in vitro transfection efficiency of gene delivery vectors based on complexes of DNA with synthetic polycations," Journal of Controlled Release 81 (2002) 201-217.
Riva, et al., "Contribution of "click chemistry" to the synthesis of antimicrobial aliphatic copolyester", Polymer (2008), vol. 49, iss. 8, pp. 2023-2028. Available online Mar. 7, 2008.
Riva, et al., "Contribution of "click chemistry" to the synthesis of antimicrobial aliphatic copolyester," Polymer 49 (2008) 2023-2028; available online Mar. 7, 2008.
Seow, et al., "Functional polycarbonates and their self-assemblies as promising non-viral vectors", J. of Controll. Release (2009) pp. 1-8.
Sigma-Aldrich, "Polyethylenimine (PEI)-Poly(2-oxazoline) and Polyethylenimine (PEI) Sigma-Aldrich", Retrieved from the Internet at URL: http://www.sigmaaldrich.com/materials-science/material-science-products.html?TablePage=112434545. Retrieved Jun. 13, 2014.
Vroman, et al., "Copolymers of e-caprolactone and quaternized e-caprolactone as gene carriers," Journal of Controlled Release 118 (2007) 136-144; Available online Dec. 12, 2006.
Vroman, et al., "PEGylated quaternized copolymer/DNA complexes for gene delivery," International Journal of Pharmaceutics 344 (2007) 88-95; Available online Jul. 3, 2007.
Wang et al., "Polyethylenimine-grafted polycarbonates as biodegradable polycations for gene delivery", Biomaterials 30 (2009) pp. 4824-4832.
Wang, et al., "Synthesis, characterization and surface modification of low moduli poly(ether carbonate urethane)ureas for soft tissue engineering", J. Acta Biomaterialia, 2009, pp. 1-12.
Wiltshire, et al., "Degradable Core Cross-Linked Star Polymers via Ring-Opening Polymerization," Macromolecules, 2006, 39 (13), 4282-4285.
Wolfert, et al., "Polyelectrolyte Vectors for Gene Delivery: Influence of Cationic Polymer on Biophysical Properties of Complexes Formed with DNA," Bioconjugate Chem. 1999, 10, 993-1004; Published on Web Oct. 23, 1999.
Xiong, et al., "Synthesis of PEG-Armed and Polyphosphoester Core-Cross-Linked Nanogel by One-Step Ring-Opening Polymerization," Macromolecules, 2009, 42 (4), 893-896.

(56) References Cited

OTHER PUBLICATIONS

Yudovin-Farber, et al., "Quaternary Ammonium Polysaccharides for Gene Delivery," Bioconjugate Chem. 2005, 16, 1196-1203; Published on Web Aug. 27, 2005.

Zhang et al., "Amphiphilic Triblock Copolycarbonates with Poly(glycerol carbonate) as Hydrophilic Blocks", J. Macromolecules 2009, 42, pp. 1010-1016.

Zhao, et al., "PLGA-(L-Asp-alt-diol)x-PLGAs with Different Contents of Pendant Amino Groups: Synthesis and Characterization," Macromol. Biosci. 2005, 5, 636-643.

Zhou, et al., "Water-Soluble Poly(ethylenimine)-Based Nitric Oxide Donors: Preparation, Characterization, and Potential Application in Hemodialysis", Biomacromolecules, vol. 7, No. 9, Sep. 1, 2006 (Sep. 1, 2006), pp. 2565-2574.

Rao, N. M., "Cationic lipid-mediated nucleic acid delivery: beyond being cationic," Chemistry and Physics of Lipids, vol. 163, Issue 3, Mar. 2010, pp. 245-252.

Zaggia et al., "Synthesis and Application of Perfluoroalkyl Quaternary Ammonium Salts in Protein-Based Fire-Fighting Foam Concentrates," J. Surfact. Deterg. (2010), 13, pp. 33-40.

USPTO, Non-Final Office Action, U.S. Appl. No. 12/645,931, dated Mar. 22, 2012.

USPTO, Final Office Action, U.S. Appl. No. 12/645,931, dated Jan. 2, 2013.

USPTO, Final Office Action, U.S. Appl. No. 12/645,931, dated Aug. 8, 2014.

USPTO, Non-Final Office Action, U.S. Appl. No. 12/646,024, dated Oct. 25, 2012.

USPTO, Non-Final Office Action, U.S. Appl. No. 13/619,958, dated Jul. 14, 2015.

Ong et al., "Biodegradable cationic poly(carbonates): effect of varying side chain hydrophobicity on key aspects of gene transfection,", Acta Biomaterialia, vol. 54, May 2017, pp. 201-211.

Yang et al., "Novel Biodegradable Block Copolymers of Polyethylene glycol) (PEG) and Cationic Polycarbonate Effects of PEG Configuration on Gene Delivery," Macromol. Rapid Commun. 2011, 32, 1826-1833.

\* cited by examiner

BIODEGRADABLE POLYMERS, COMPLEXES THEREOF FOR GENE THERAPEUTICS AND DRUG DELIVERY, AND METHODS RELATED THERETO

BACKGROUND

The present invention relates to biodegradable polymers, and more specifically, complexes thereof with biologically active molecules, for use in gene therapeutics and drug delivery.

Recent advances in gene therapeutics have lead to a critical need for a broader selection of less expensive, non-cytotoxic carrier materials for gene transfection. The carrier materials should package and protect a genetic cargo in the extracellular environment, transport it across the cell membrane, and release the cargo within the cell at a suitable point. Carrier materials are typically classified into viral vectors and non-viral vectors. Viral vectors have excellent efficiencies in delivery and expression of genes. However, they often cause immunologically adverse responses, are expensive to produce, and are limited with respect to gene encapsulation.

Non-viral vectors include cationic polymers and cationic lipids (lipoplex). These materials have drawn increasing attention as alternatives to viral vectors owing to their potentially low production costs and flexibility with respect to molecular design. Cationic polymers and cationic lipids can bind electrostatically to negatively charged genetic material to form a carrier-gene complex having decreased net charge. These complexes can potentially facilitate effective transfection of genetic material into a cell.

Ideally the polymer-gene complex should enter the cytoplasm of the cell by endocytosis. The complex must escape from the acidic endosomal environment into the cytosol before infusing into lysosomes where enzymes can decompose the genes. A key design feature for such behavior is the tuning of amine residues of the polymer carrier to provide buffering capacity, which leads to osmotic swelling and rupture of the endosome, freeing the bio-active cargo and/or the bio-active cargo-carrier complex (i.e., polyplex) into the cytoplasm (proton sponge hypothesis), and thus enabling gene transfection. For example, the free amine residues on the cationic polymer such as poly(ethylene imine) (PEI) can effectively buffer the protons in the endosome, causing osmotic swelling and rupture of the endosome. PEI is recognized as a good non-viral vector having superior transfection efficiency. This is attributed to its high charge density, which facilitates formation of a compacted complex, and its high density of near-neutral secondary amine sites, which provide buffering capacity. However, PEI is not biodegradable and it is also considered highly cytotoxic. Thus, a challenge in the design of synthetic transfection vectors based on cationic polymers is achieving low cytotoxicity and high transfection efficiency. Poly(beta-amino ester)s (PBAEs), modified PEIs, poly(amino acid)s, poly(beta-aminosulfonamide)s (PBASs), dendrimers based on poly(L-lysine) (PLL), and poly(amidoamine) (PAMAM) dendrimers have been reported as efficient non-viral vectors for safe gene delivery. These polymers, however, have several issues to be solved, especially in the synthetic process. PBAEs and PBASs prepared by polycondensation have relatively broad molecular weight distributions, PEI and its derivatives usually contain some branched structures that are difficult to control, dendrimers require multiple steps to generate desirable molecular weight, and polymers based on amino acids have high production costs due to expensive starting materials.

Polymer-gene complexation via electrostatic interactions is an effective transporting and protection strategy for genetic material, however this tight packing also presents a problem in the unpacking of genes. Numerous strategies have been explored to facilitate the release of the bio-active cargo including degradable systems, reversible crosslinking, modestly charged cationic polymers, hierarchical self-assembled pH-responsive terpolymers and a number of charge shifting strategies.

A continued need exists for less expensive, less cytotoxic, more biodegradable synthetic carriers for gene transfection and drug delivery. The carriers should have predictable molecular weight and low polydispersity, and form reversible extracellular complexes with bio-active molecules, particularly nucleotides.

SUMMARY

Accordingly, in an embodiment, a biodegradable cationic polymer is disclosed, comprising:

first repeat units derived from a first cyclic carbonyl monomer by ring-opening polymerization, wherein more than 0% of the first repeat units comprise a side chain moiety comprising a quaternary amine group;

a subunit derived from a monomeric diol initiator for the ring-opening polymerization; and an optional endcap group.

In another embodiment, a method of forming a biodegradable cationic polymer is disclosed, comprising:

forming a first mixture comprising a first cyclic carbonyl monomer, a catalyst, an accelerator, a monomeric diol initiator, and an optional solvent, wherein the first cyclic carbonyl monomer comprises a monovalent leaving group capable of reacting with a tertiary amine to form a quaternary amine;

forming a first polymer comprising first repeat units derived from the first cyclic carbonyl monomer by ring-opening polymerization;

optionally endcapping the first polymer to form a precursor polymer; and treating the precursor polymer with the tertiary amine to form the cationic polymer, wherein more than 0% of the first repeat units derived from the first cyclic carbonyl monomer comprise a side chain moiety comprising a quaternary amine.

In another embodiment, a method of forming a biodegradable cationic block copolymer is disclosed, comprising:

forming a reaction mixture comprising a catalyst, an accelerator, a monomeric diol initiator, and an optional solvent;

sequentially adding to the reaction mixture and reacting by ring-opening polymerization a first cyclic carbonyl monomer followed by a second cyclic carbonyl monomer, thereby forming a first block copolymer, wherein the first cyclic carbonyl monomer comprises a monovalent leaving group capable of reacting with a tertiary amine to form a quaternaray amine, and the second cyclic carbonyl monomer is not capable of reacting with the tertiary amine to form any quaternary amine;

optionally endcapping the first block copolymer, thereby forming a precursor block copolymer; and treating the precursor block copolymer with a tertiary amine to form the cationic polymer, wherein the cationic polymer comprises first repeat units derived from the first cyclic carbonyl monomer, and more than 0% of the first repeat units comprise a side chain moiety comprising the quaternary amine.

In another embodiment, a polymer complex is disclosed, comprising:
   a negatively charged biologically active material; and
   a biodegradable cationic polymer, comprising:
      first repeat units derived from a first cyclic carbonyl monomer by ring-opening polymerization, wherein more than 0% of the first repeat units comprise a side chain moiety comprising a quaternary amine group;
      a subunit derived from a monomeric diol initiator for the ring-opening polymerization; and
      an optional endcap group.

In another embodiment, a method of forming a polymer complex for treating a cell is disclosed, comprising:
   contacting a first aqueous mixture comprising a biodegradable cationic polymer with a second aqueous mixture comprising a negatively charged biologically active material to form a third aqueous mixture comprising the polymer complex, wherein the biodegradable cationic polymer comprises: first repeat units derived from a first cyclic carbonyl monomer by ring-opening polymerization, a subunit derived from a monomeric diol initiator for the ring-opening polymerization, and an optional endcap group, wherein more than 0% of the first repeat units comprise a side chain moiety comprising a quaternary amine group.

In another embodiment, a method of treating a cell is disclosed, comprising:
   contacting the cell with nanoparticles of a polymer complex comprising a biodegradable cationic polymer and a negatively charged biologically active material; wherein the biodegradable cationic polymer comprises: first repeat units derived from a first cyclic carbonyl monomer by ring-opening polymerization, a subunit derived from a monomeric diol initiator for the ring-opening polymerization, and an optional endcap group, wherein more than 0% of the first repeat units comprise a side chain moiety comprising a quaternary amine group.

The above-described and other features and advantages of the present invention will be appreciated and understood by those skilled in the art from the following detailed description, drawings, and appended claims.

DETAILED DESCRIPTION

Figure 1:
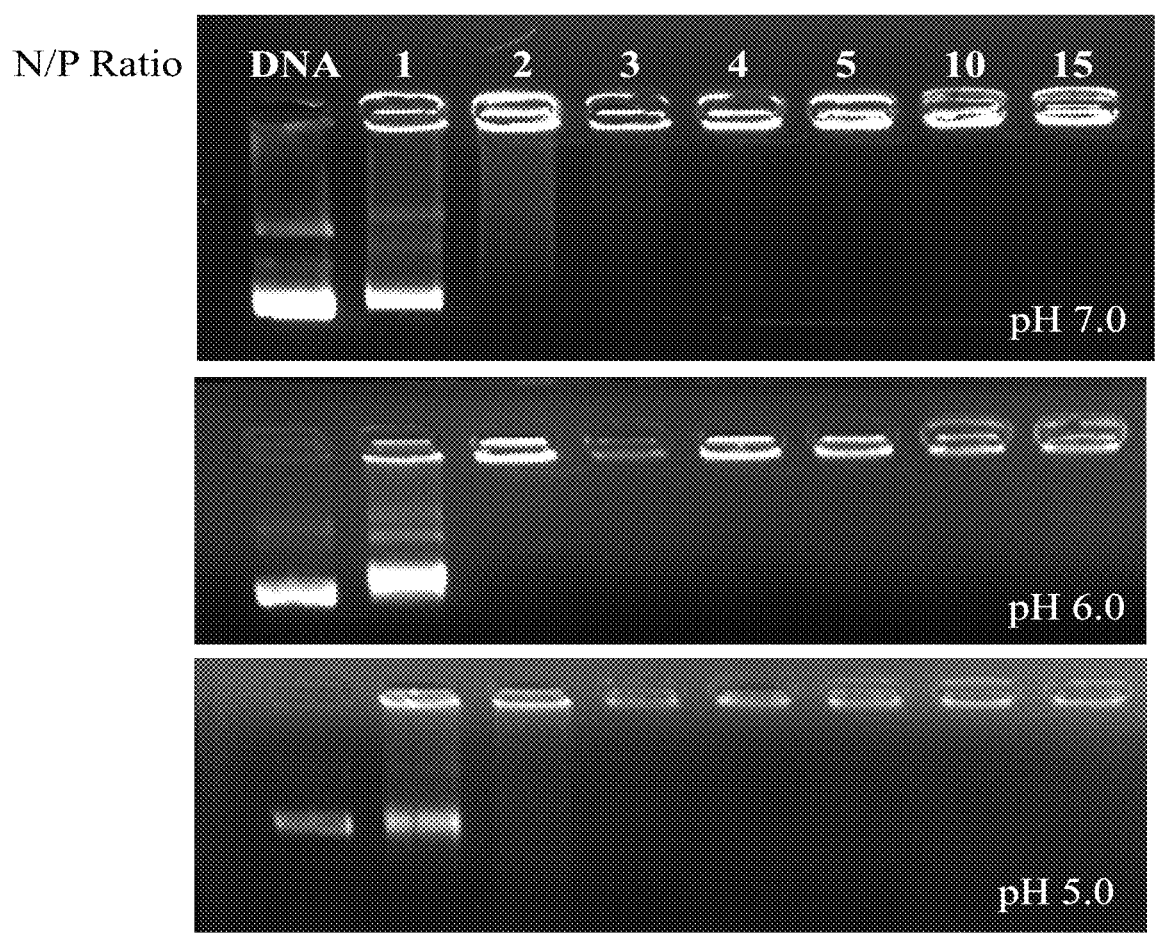
FIG. 1 is a photographic image agarose gel electrophoresis experiments at different pH and at various N/P ratios of polyplexes prepared with the cationic polymer of Example 15 and DNA.

Biodegradable cationic polymers are disclosed that form nano-sized complexes with biologically active molecules and are less cytotoxic than other carriers such as poly (ethylene imine) (PEI). The cationic polymers are derived by ring-opening polymerization (ROP) of a first cyclic carbonyl monomer having a monovalent leaving group, such as an alkyl halide or sulphonate ester, which is capable of reacting with a tertiary amine to form a moiety comprising a quaternary amine. Other cyclic carbonyl monomers are selected as diluents for the former, to provide hydrophobicity, and/or to provide charge shifting capability to the polymer. The cationic polymers can be densely charged and thus freely soluble in water, or possess amphiphilic properties, forming nanoparticles in aqueous solution. The ring-opening method allows precise control of the molecular weight of the polymer, achieves a low polydispersity, and is compatible with a variety of functional groups. The reaction with the tertiary amine to form the moiety comprising a quaternary amine can be performed before or after the ring-opening polymerization, more particularly after the polymerization. The quaternization is accompanied by minimal, if any, crosslinking of the cationic polymer. Examples of cyclic carbonyl monomers include cyclic carbonate monomers and lactones, including lactides, that ring-open to form polymers comprising carbonate and ester repeat units, respectively. The quaternary amine is located on the polymer side chain, and if desired can be linked directly to the polymer backbone. The positively charged quaternary amine groups provide binding strength to negatively charged biologically active materials. In an embodiment, the tertiary amine is a bis-tertiary amine, and the cationic polymer comprises a side chain moiety comprising a quaternary amine and a tertiary amine. The side chain tertiary amine groups provide buffering capacity to facilitate release of the bio-active material from the polymer complex. Other functional groups can be used to facilitate the release of the bio-active material from the polymer complex, such as secondary amine groups, citraconic amide groups, ester groups, and imine groups. The release of a bio-active material can also be facilitated by cationic polymers capable of charge-shifting. In charge shifting, the net positive charge of the cationic polymer is reduced by the conversion of a non-charged group on the cationic polymer side chain into a negatively charged group after the polymer complex has entered the cell. A cationic polymer capable of charge-shifting can comprise, for example, a latent carboxylic acid group, such as an acetal ester, in addition to the quaternary amine. Acetal esters can be hydrolyzed under the mildly acidic conditions of the endosomal environment to form a carboxylic acid group. In the more basic environment of the cytosol, the carboxylic acid groups become ionized, thereby lowering the net positive charge of the cationic polymer and allowing the release of the negatively charged bio-active material. The ring-opening polymerization of the cyclic carbonyl monomers allows for tuning of the charge-shifting capability of the cationic polymers for a specific bio-active material. The cationic polymers can be linear or branched, and can be easily modified to tune the charge and the buffering strength. With a gene, the cationic polymer forms a complex (i.e., polyplex) having an average particle size of from about 10 nm to about 250 nm.

The term "biodegradable" is defined by the American Society for Testing and Materials as a degradation caused by biological activity, especially by enzymatic action, leading to a significant change in the chemical structure of the material. For purposes herein, a material is "biodegradable" if it undergoes 60% biodegradation within 180 days in accordance with ASTM D6400.

For purposes herein, a "cargo" can be any biologically active substance that forms a reversible, nano-sized complex with the disclosed cationic polymers, with the proviso that the complex enters a cell by endocytosis, and the complex releases the biologically active substance at a desired stage within the cell. Biologically active substances include biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing. "Biologically active" means the substance can alter the chemical structure and/or activity of a cell in a desirable manner, or can selectively alter the chemical structure and/or activity of a cell type relative to another cell type in a desirable manner. As an example, one desirable change in a chemical structure can be the incorporation of a gene into the DNA of the cell. A desirable change in activity can be the expression of the transfected gene. Another change in cell activity can be the induced production of a desired hormone or enzyme. Alternatively, a desirable change in activity can be the selective death of one cell type over another cell type. No limitation is placed on the relative change in cellular activity caused by the biologically active substance, providing the change is desirable and useful. Moreover, no limitation is placed on the so-called "cargo," providing the cargo induces a useful cellular response when released from the complex.

In the following description of general formulas for cyclic carbonyl monomers, a "first cyclic carbonyl monomer" refers to a first category of cyclic carbonyl monomers comprising a monovalent leaving group capable of reacting with a tertiary amine to form a moiety comprising a quaternary amine. The term "second cyclic carbonyl monomer" refers to a second category of cyclic carbonyl monomer, that contains no monovalent leaving group capable of reacting with the tertiary amine to form a moiety comprising any quaternary amine. Otherwise, the first and second cyclic carbonyl monomers can have a structure selected from any of following described formulas.

The cyclic carbonyl monomers can be selected independently from compounds of the general formula (1):

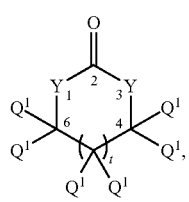
(1)

wherein t is an integer from 0 to 6, and when t is 0 carbons labeled 4 and 6 are linked together by a single bond. Each Y is a divalent radical independently selected from

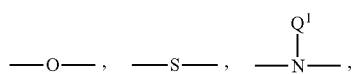

and

where the dash "-" indicates the point of attachment. The latter two groups are also expressed herein as $—N(Q^1)—$ and $—C(Q^1)_2—$. Each $Q^1$ is a monovalent radical independently selected from hydrogen, halides, carboxy groups, alkyl groups comprising 1 to 30 carbons, aryl groups comprising 6 to 30 carbon atoms, or groups having the structure

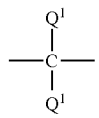

where $M^1$ is a monovalent radical selected from $—R^1$, $—OR^1$, $—NHR^1$, $—NR^1R^1$, or $—SR^1$, where the dash represents the point of attachment, and each $R^1$ is a monovalent radical independently selected from alkyl groups comprising 1 to 30 carbons, or aryl groups comprising 6 to 30 carbons. One or more $Q^1$ groups can further comprise a monovalent leaving group capable of reacting with a tertiary amine to form a moiety comprising a quaternary amine (i.e., a positive charged quaternary ammonium ion bonded to four carbons). Non-limiting examples of monovalent leaving groups include halides in the form of an alkyl halide (e.g., alkyl chloride, alkyl bromide, or alkyl iodide), sulphonate esters (e.g., tosylate or mesylate esters), and epoxides. Each $Q^1$ group can independently be branched or non-branched. Each $Q^1$ group can also independently comprise additional functional groups, including a ketone group, aldehyde group, alkene group, alkyne group, cycloaliphatic ring comprising 3 to 10 carbons, heterocylic ring comprising 2 to 10 carbons, ether group, amide group, ester group, and combinations of the foregoing additional functional groups. The heterocyclic ring can comprise oxygen, sulfur and/or nitrogen. Two or more $Q^1$ groups can together form a ring. A first cyclic carbonyl monomer of formula (1) comprises one or more $Q^1$ groups comprising a monovalent leaving group capable of reacting with a tertiary amine to form a moiety comprising a quaternary amine. A second cyclic carbonyl monomer of formula (1) comprises no functional group capable of reacting with the tertiary amine to form a moiety comprising any quaternary amine.

A more specific cyclic carbonyl monomer capable of ring-opening polymerization has the general formula (2):

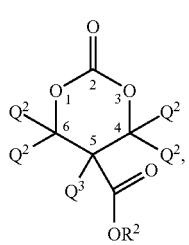
(2)

wherein $Q^2$ is a monovalent radical independently selected from the group consisting of hydrogen, halides, carboxy groups, alkyl groups comprising 1 to 30 carbons, aryl groups comprising 6 to 30 carbon atoms, and groups having the structure

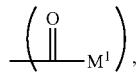

wherein $M^1$ is a monovalent radical selected from $—R^1$, $—OR^1$, $—NHR^1$, $—NR^1R^1$, or $—SR^1$, wherein each $R^1$ is a monovalent radical independently selected from the group consisting of alkyl groups comprising 1 to 30 carbons, and aryl groups comprising 6 to 30 carbons; $R^2$ is a monovalent radical independently selected from the group consisting of alkyl groups comprising 1 to 30 carbons, and aryl groups comprising 6 to 30 carbons; and $Q^3$ is a monovalent radical selected from the group consisting of hydrogen, alkyl groups having 1 to 30 carbons, and aryl groups having 6 to 30 carbons. In an embodiment, each $Q^2$ is hydrogen, $Q^3$ is a methyl or ethyl group, and $R^2$ is an alkyl group comprising 1 to 30 carbons. A first cyclic carbonyl monomer of formula (2) comprises an $R^2$ group comprising a monovalent leaving group capable of reacting with a tertiary amine to form a moiety comprising a quaternary amine. A second cyclic carbonyl monomer of formula (2) comprises no functional group capable of reacting with the tertiary amine to form a moiety comprising any quaternary amine.

Another more specific cyclic carbonyl monomer has the general formula (3):

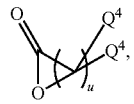

(3)

wherein each $Q^4$ is a monovalent radical independently selected from the group consisting of hydrogen, halides, carboxy groups, alkyl groups comprising 1 to 30 carbons, aryl groups comprising 6 to 30 carbon atoms, and groups having the structure

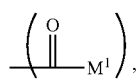

where $M^1$ is a monovalent radical selected from $—R^1$, $—OR^1$, $—NHR^1$, $—NR^1R^1$, or $—SR^1$, wherein each $R^1$ is a monovalent radical independently selected from the group consisting of alkyl groups comprising 1 to 30 carbons, and aryl groups comprising 6 to 30 carbons; and u is an integer from 1 to 8. The lactone ring can optionally comprise a carbon-carbon double bond; that is, optionally, a

group of formula (3) can independently represent a

group. The lactone ring can also comprise a heteroatom such as oxygen, nitrogen, sulfur, or a combination thereof; that is, optionally a

group of formula (3) can independently represent a $—O—$, $—S—$, $—NHR^1$, or an $—NR^1R^1$ group, wherein $R^1$ has the same definition as above. A first cyclic carbonyl monomer of formula (3) comprises one or more $Q^4$ groups comprising a monovalent leaving group capable of reacting with a tertiary amine to form a moiety comprising a quaternary amine. A second cyclic carbonyl monomer of formula (3) comprises no functional group capable of reacting with the tertiary amine to form a moiety comprising any quaternary amine. In an embodiment, u is an integer from 1 to 6 and each $Q^4$ is hydrogen.

Another more specific cyclic carbonyl monomer is a dioxane dicarbonyl of the general formula (4):

(4)

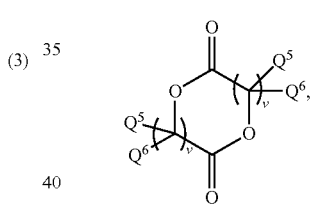

wherein each $Q^5$ is a monovalent radical independently selected from the group consisting of hydrogen, halides, carboxy groups, alkyl groups comprising 1 to 30 carbons, aryl groups comprising 6 to 30 carbon atoms, and groups having the structure

where $M^1$ is a monovalent radical selected from $—R^1$, $—OR^1$, $—NHR^1$, $—NR^1R^1$, or $—SR^1$, wherein each $R^1$ is a monovalent radical independently selected from the group consisting of alkyl groups comprising 1 to 30 carbons, and aryl groups comprising 6 to 30 carbons; each $Q^6$ is a monovalent group independently selected from the group consisting of hydrogen, alkyl groups having 1 to 30 carbons, and aryl groups having 6 to 30 carbons; and each v is independently an integer from 1 to 6. A first cyclic carbonyl monomer of formula (4) comprises one or more $Q^5$ groups and/or a $Q^6$ groups comprising a monovalent leaving group capable of reacting with a tertiary amine to form a moiety comprising a quaternary amine. A second cyclic carbonyl monomer of formula (4) comprises no functional group capable of reacting with the tertiary amine to form a moiety comprising any quaternary amine. In an embodiment, each v is 1, each $Q^5$ is hydrogen, and each $Q^6$ is an alkyl group comprising 1 to 6 carbons.

The cyclic carbonyl compounds can have one or more asymmetric carbon centers that can be present in isomerically enriched form, either as an R-isomer or an S-isomer. Further, each asymmetric carbon center can independently be present in an enantiomeric excess of 80% or more, more specifically 90%.

Examples of cyclic carbonyl monomers of formulas (1) or (2) having a monovalent leaving group in the form of an alkyl halide include the cyclic monomers of Table 1.

TABLE 1

(MTCOPrCl)

(MTCOPrBr)

(MTCOEtI)

Additional examples of cyclic carbonyl monomers of formula (2) include the compounds of Table 2. These can be used, for example, as co-monomers in the ring-opening polymerization of the halide monomers of Table 1, to form random copolymers or block copolymers.

TABLE 2

$[CH_2]m$ m = 1, Trimethylene carbonate, (TMC)
m = 2, Tetramethylene carbonate, (TEMC)
m = 3, Pentamethylene carbonate, (PMC)

TABLE 2-continued

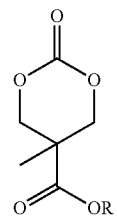

R = hydrogen, (MTCOH)
R = methyl, (MTCOMe)
R = t-butyl, (MTCO$^t$Bu)
R = ethyl, (MTCOEt)

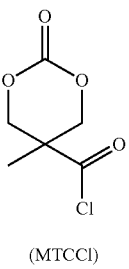

(MTCCl)

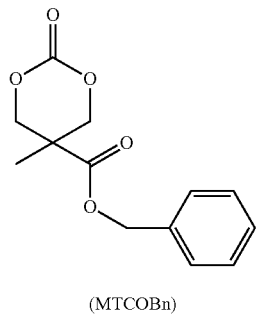

(MTCOBn)

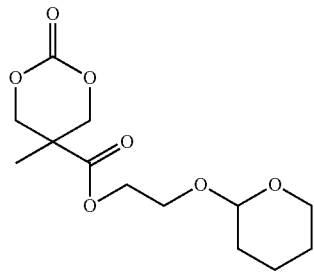 [SMILES: CC1(C(=O)OCCOC2CCCCO2)COC(=O)OC1]

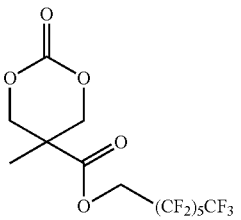

TABLE 2-continued
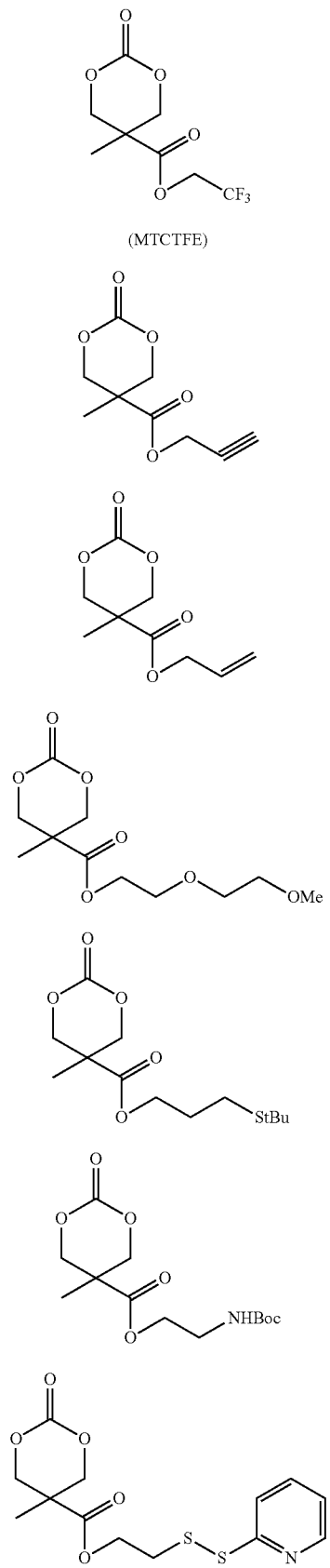
(MTCTFE)
TABLE 2-continued
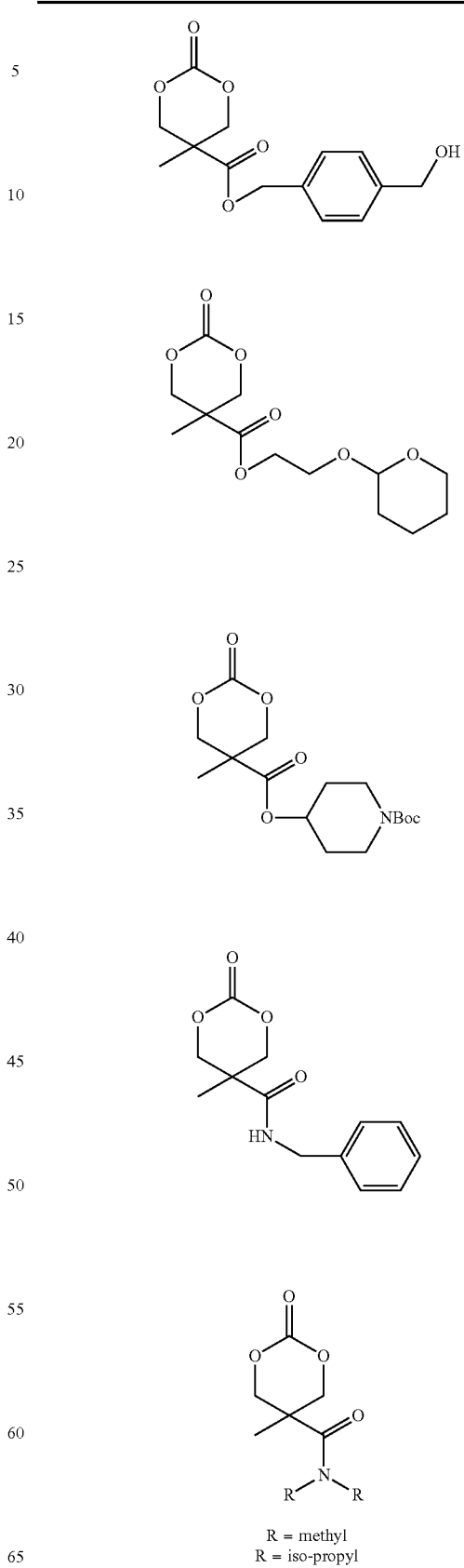
R = methyl
R = iso-propyl Examples of cyclic carbonyl monomers of formula (3) include the compounds of Table 3.

TABLE 3

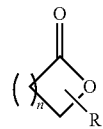

R = H; n = 1: beta-Propiolactone, (b-PL)
R = H; n = 2: gamma-Butyrolactone, (g-BL)
R = H; n = 3: delta-Valerolactone, (d-VL)
R = H; n = 4: epsilon-Caprolactone, (e-CL)
R = CH$_3$; n = 1: beta-Butyrolactone, (b-BL)
R = CH$_3$; n = 2: gamma-Valerolactone, (g-VL)

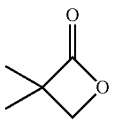

Pivalolactone
(PVL)

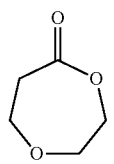

1,5-Dioxepan-2-one
(DXO)

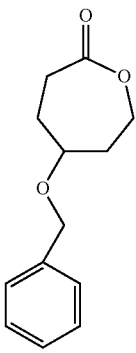 [SMILES: O=C1CCC(OCc2ccccc2)CCO1]

5-(Benzyloxy)oxepan-2-one
(BXO)

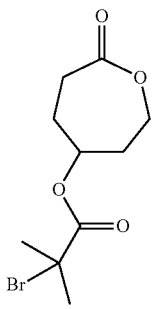

7-Oxooxepan-4-yl 2-bromo-2-methylpropanoate
(BMP-XO)

TABLE 3-continued

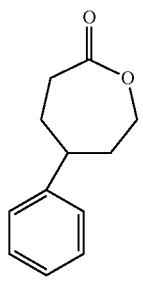 [SMILES: O=C1CCC(c2ccccc2)CCO1]

5-Phenyloxepan-2-one
(PXO)

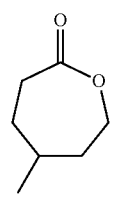

5-Methyloxepan-2-one
(MXO)

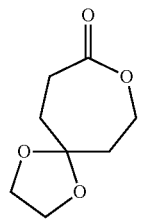 [SMILES: O=C1CCC2(CCO1)OCCO2]

1,4,8-Trioxa(4,6)spiro-9-undecane
(TOSUO)

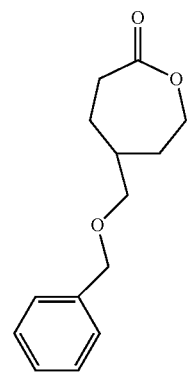 [SMILES: O=C1CCC(COCc2ccccc2)CCO1]

5-(Benzyloxymethyl)oxepan-2-one
(BOMXO)

TABLE 3-continued

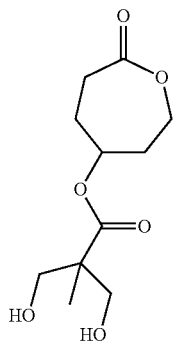 [SMILES: CC(CO)(CO)C(=O)OC1CCOC(=O)CC1]

7-Oxooxepan-4-yl 3-hydroxy-2-
(hydroxymethyl)-2-methylpropanoate
(OX-BHMP)

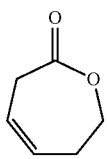

(Z)-6,7-Dihydrooxepin-2(3H)-one
(DHXO)

Examples of cyclic carbonyl monomers of formula (4) include the compounds of Table 4.

TABLE 4

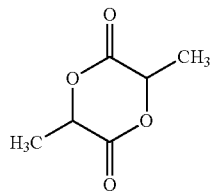

D-Lactide, (DLA),
L-Lactide, (LLA), or
racemic Lactide, 1:1 D:L forms, (DLLA)

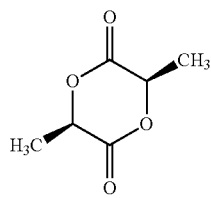

meso-Lactide, (MLA)
(two opposite centers of asymmetry,
R and S)

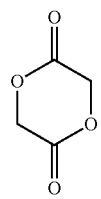

Glycolide
(GLY)

As stated above, complexation via electrostatic interactions is an effective packaging strategy for genetic material; however, post-transfection release is often difficult and hence transfection rates can be low. To circumvent this problem a charge-shifting strategy can be utilized, wherein the cyclic carbonyl monomer comprises a latent carboxylic acid group. By this is meant that the cationic polymer comprises a pendant protected carboxylic acid that can be converted to a carboxylic acid at about pH 5, corresponding to the pH of the endosomal environment. An example of a latent carboxylic acid group is an acetal-protected carboxylic acid group, herein also referred to as an acetal ester group. The acetal ester group has the general formula (5)

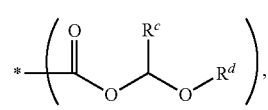

(5)

wherein *- represents the bond to a cyclic carbonyl moiety, and $R^c$ and $R^d$ are monovalent radicals independently comprising from 1 to 20 carbons. In an embodiment, $R^c$ is methyl and $R^d$ is ethyl. In another embodiment, the second cyclic carbonyl monomer is MTCOEE:

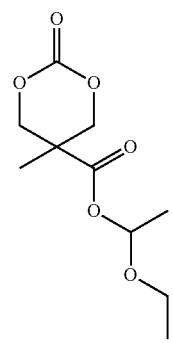

(MTCOEE)

When copolymerized into the cationic polymer, repeat units derived from MTCOEE comprise a side chain acetal ester that is readily deprotected in the acidic endosomal environment. Once released into the cytoplasm, the resulting carboxylic acid groups of the cationic polymer can be deprotonated, thus neutralizing the net charge on the carrier and potentially facilitating the release of the bio-active material. Cationic polymers derived from MTCOEE are capable of binding DNA to form self-assembled nanoparticles having an average diameter of between 90 and 110 nm.

Another strategy for facilitating endosomal release involves non-covalent interactions to stabilize a bio-active cargo, for example, using cyclic carbonyl monomers comprising a fluorinated tertiary alcohol group. Fluorinated tertiary alcohol groups are known to bind to phosphates and related structures, but with interaction energies that are lower than electrostatic interactions, and hence more easily released.

The above monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

The above-described cyclic carbonyl monomers, at least one of which comprises a monovalent leaving group capable of reacting with the tertiary amine to form a quaternary amine, undergoes ring-opening polymerization to form a first polymer. The first polymer is a living polymer capable of initiating chain growth with the same or a different cyclic carbonyl monomer, or a mixture of cyclic carbonyl monomers, to form a block copolymer. The first polymer is optionally treated with an endcapping agent to prevent further chain growth and to stabilize the reactive end groups. The resulting precursor polymer is then treated with a tertiary amine to form the cationic polymer. The first polymer, the precursor polymer, and the cationic polymer can be produced in atactic, syndiotactic or isotactic forms. The particular tacticity depends on the cyclic monomer(s), isomeric purity, and the reaction conditions.

Alternatively, the cationic polymer can be obtained by ring-opening polymerization of a cyclic carbonyl monomer comprising a quaternary amine group and a tertiary amine group. However, these monomers are more difficult to prepare, are less stable, and the corresponding polymers tend to be more polydisperse. Therefore, the quaternization reaction is performed after the ring-opening polymerization.

In the simplest example, the first polymer is a homopolymer prepared from a reaction mixture comprising a first cyclic carbonyl monomer comprising a monovalent leaving group capable of reacting with the tertiary amine to form a moiety comprising a quaternary amine, a catalyst, an accelerator, a monomeric diol initiator, and an optional solvent. In an embodiment, the catalyst and the accelerator are the same material. For example, some ring opening polymerizations can be conducted using 1,8-diazabicyclo[5.4.0]undec-7-ene (DBU) alone, with no another catalyst. The ring-opening polymerization is generally conducted in a reactor under inert atmosphere such as nitrogen or argon. The polymerization can be performed by solution polymerization in an inactive solvent such as benzene, toluene, xylene, cyclohexane, n-hexane, dioxane, chloroform and dichloroethane, or by bulk polymerization. The ROP reaction temperature can be from about ambient temperature to 250° C. Generally, the reaction mixture is heated at atmospheric pressure for 0.5 to 72 hours to effect polymerization, forming a second mixture comprising the first polymer. A subunit derived from the monomeric diol initiator is attached to an end of each ring opened polymer chain grown therefrom. The first polymer is then optionally endcapped to form a precursor polymer. The precursor polymer is then treated with a tertiary amine to form the cationic polymer, wherein more than 0% of repeat units derived from the first carbonyl monomer comprise a side chain moiety comprising a quaternary amine.

The first polymer can also be a random copolymer formed by the ring opening polymerization of a mixture comprising, for example, a first cyclic carbonyl monomer and a hydrophobic second cyclic carbonyl monomer. The random first polymer can be endcapped to form a random precursor copolymer. In this case, the subunit derived from the initiator, and the terminal repeat unit comprising an endcap group, can be linked to a repeat unit derived from either monomer. The random precursor copolymer is then treated with a tertiary amine to form a random cationic copolymer, wherein more than 0% of the repeat units derived from the first cyclic carbonyl monomer comprise a moiety comprising a quaternary amine. The repeat units derived from the second cyclic carbonyl monomer do not comprise a monovalent leaving group capable of reacting with the tertiary amine to form any quaternary amine. It is understood that the reaction mixture can include additional cyclic carbonyl monomers if desired, of the first category and/or the second category.

More particularly, the first polymer is a block copolymer, formed by the sequential ring-opening polymerization of, for example, a first cyclic carbonyl monomer and a hydrophobic second cyclic carbonyl monomer, to form a first block copolymer. The first block copolymer is then optionally endcapped to form a precursor block polymer. The precursor block polymer is then treated with a tertiary amine to form a cationic block copolymer, wherein more than 0% of the repeat units derived from the first cyclic carbonyl monomer comprise a side chain moiety comprising a quaternary amine. As before, the repeat units derived from the second cyclic carbonyl monomer not comprise a monovalent leaving group capable of reacting with the tertiary amine to form a quaternary amine. Depending on the sequence order of the ring opening polymerizations, the subunit derived from the monomeric diol initiator can be attached to first repeat units derived from the first cyclic carbonyl monomer, or to second repeat units derived from the second carbonyl monomer. In one example, the first cyclic carbonyl monomer is polymerized first to form a first block of the block copolymer, and the second cyclic carbonyl monomer is polymerized second to form a second block of the block copolymer. In this example, the cationic block copolymer comprises a hydrophilic core block derived from the first cyclic carbonyl monomer, which is attached to the subunit derived from the monomeric diol initiator, and a hydrophobic outer block derived from the second carbonyl monomer, which is optionally endcapped. In another example, the second cyclic carbonyl monomer is polymerized first, and the first cyclic carbonyl monomer is polymerized second. In this example, the cationic block copolymer comprises a hydrophobic core block comprising second repeat units attached to the subunit derived from the diol initiator, and a hydrophilic outer block, which is optionally endcapped. If desired, additional blocks can be grown from the living ends of the non-encapped chains using the first cyclic carbonyl monomer, the second cyclic carbonyl monomer, a different cyclic carbonyl monomer, or combinations thereof. The block copolymers are amphiphilic, forming self-assembled nano-sized particles in aqueous solution.

Exemplary catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetra-ethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; tertiary amines such as triallylamine, triethylamine, tri-n-octylamine and benzyldimethylamine; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate. More particularly, the catalyst is zirconium octanoate, tetraalkoxy zirconium or a trialkoxy aluminum compound.

Other ROP catalysts include metal-free organocatalysts that can provide a platform to polymers having controlled, predictable molecular weights and narrow polydispersities. Examples of organocatalysts for the ROP of cyclic esters, carbonates and siloxanes are 4-dimethylaminopyridine, phosphines, N-heterocyclic carbenes (NHC), bifunctional aminothioureas, phosphazenes, amidines, and guanidines. In an embodiment the catalyst is N-(3,5-trifluoromethyl)phenyl-N'-cyclohexyl-thiourea (TU):

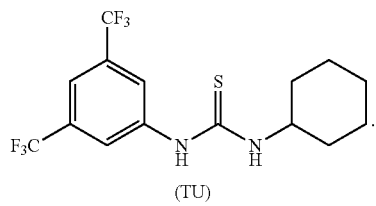

(TU)

Another metal-free ROP catalyst comprises at least one 1,1,1,3,3,3-hexafluoropropan-2-ol-2-yl (HFP) group. Singly-donating hydrogen bond catalysts have the formula (6):

$$R^2-C(CF_3)_2OH \qquad (6).$$

$R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 5.

TABLE 5

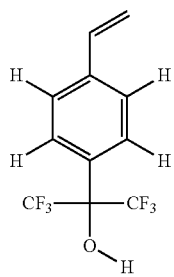

4-HFA-St

TABLE 5-continued

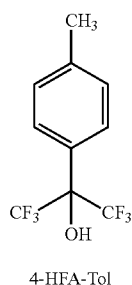

4-HFA-Tol

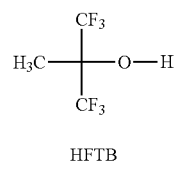

HFTB

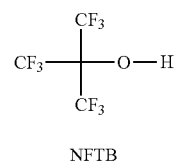

NFTB

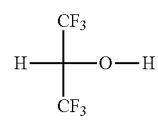

HFIP

Doubly-donating hydrogen bonding catalysts have two HFP groups, represented by the general formula (7):

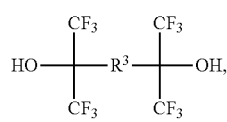

(7)

wherein $R^3$ is a divalent radical bridging group containing from 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (7) include those listed in Table 6. In a specific embodiment, $R^2$ is an arylene or substituted arylene group, and the HFP groups occupy positions meta to each other on the aromatic ring.

TABLE 6

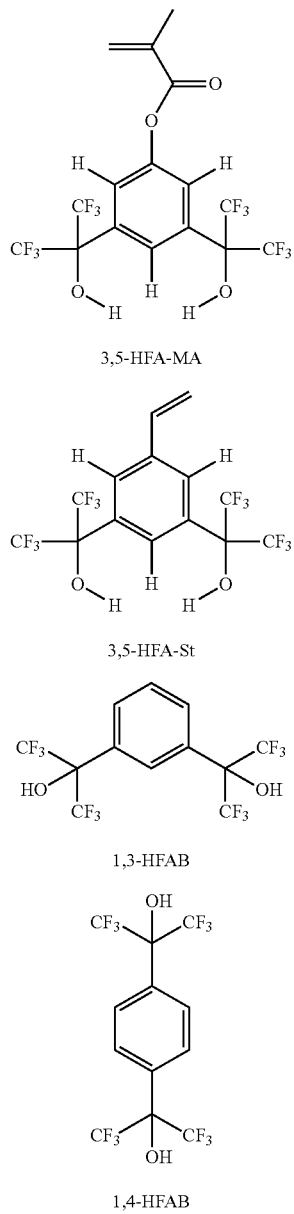

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Typical examples of such polymerizeable HFP-containing monomers may be found in: Ito et al., *Polym. Adv. Technol.* 2006, 17(2), 104-115, Ito et al., *Adv. Polym. Sci.* 2005, 172, 37-245, Ito et al., US20060292485, Maeda et al. WO2005098541, Allen et al. US20070254235, and Miyazawa et al. WO2005005370. Alternatively, pre-formed polymers and other solid support surfaces can be modified by chemically bonding an HFP-containing group to the polymer or support via a linking group. Examples of such polymers or supports are referenced in M. R. Buchmeiser, ed. "Polymeric Materials in Organic Synthesis and Catalysis," Wiley-VCH, 2003, M. Delgado and K. D. Janda "Polymeric Supports for Solid Phase Organic Synthesis," *Curr. Org. Chem.* 2002, 6(12), 1031-1043, A. R. Vaino and K. D. Janda "Solid Phase Organic Synthesis: A Critical Understanding of the Resin", *J. Comb. Chem.* 2000, 2(6), 579-596, D. C. Sherrington "Polymer-supported Reagents, Catalysts, and Sorbents: Evolution and Exploitation—A Personalized View," *J. Polym. Sci. A. Polym. Chem.* 2001, 39(14), 2364-2377, and T. J. Dickerson et al. "Soluble Polymers as Scaffold for Recoverable Catalysts and Reagents," *Chem. Rev.* 2002, 102(10), 3325-3343. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one catalyst and, when appropriate, several catalysts together. The ROP catalyst is added in a proportion of 1/20 to 1/40,000 moles relative to the cyclic carbonyl monomers, and preferably of 1/1,000 to 1/20,000 moles.

The ring-opening polymerization is conducted in the presence of an accelerator, in particular a nitrogen base. Exemplary nitrogen base accelerators are listed below and include pyridine (Py), N,N-dimethylaminocyclohexane ($Me_2NCy$), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4, 5-dihydroimidazol-2-ylidene (Im-8) or a combination thereof, shown in Table 7.

TABLE 7

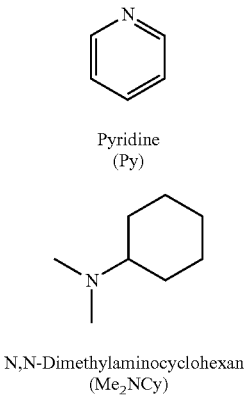

Pyridine
(Py)

N,N-Dimethylaminocyclohexane
($Me_2NCy$)

TABLE 7-continued

4-N,N-Dimethylaminopyridine
(DMAP)

trans 1,2-Bis(dimethylamino)cyclohexane
(TMCHD)

1,8-Diazabicyclo[5.4.0]undec-7-ene
(DBU)

7-Methyl-1,5,7-triazabicyclo[4.4.0]dec-5-ene
(MTBD)

1,5,7-Triazabicyclo[4.4.0]dec-5-ene
(TBD)

(−)-Sparteine
(Sp)

1,3-Bis(2-propyl)-4,5-dimethylimidazol-2-ylidene
(Im-1)

1,3-Bis(2,4,6-trimethylphenyl)imidazol-2-ylidene
(Im-2)

1,3-Bis(2,6-di-i-propylphenyl(imidazol-2-ylidene
(Im-3)

1,3-Bis(1-adamantyl)imidazol-2-yliden)
(Im-4)

1,3-Di-i-propylimidazol-2-ylidene
(Im-5)

1,3-Di-t-butylimidazol-2-ylidene
(Im-6)

1,3-Bis(2,4,6-trimethylphenyl)-4,5-dihydroimidazol-2-ylidene
(Im-7)

TABLE 7-continued

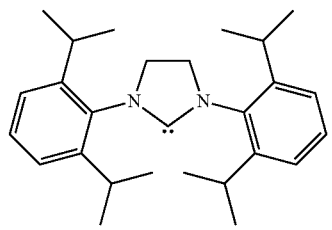

1,3-Bis(2,6-di-i-propylphenyl)-4,5-
dihydroimidazol-2-ylidene
(Im-8)

In one embodiment, the accelerator has two or three nitrogens, each capable of participating as a Lewis base, as for example in the structure (−)-sparteine. Stronger bases generally improve the polymerization rate.

The ROP reaction mixture also comprises an initiator. Initiators generally include nucleophiles such as alcohols, amines and thiols. The initiator can be monofunctional, difunctional or multifunctional such as dendritic, polymeric or related architectures. Monofunctional initiators can include nucleophiles with protected functional groups that include thiols, amines, acids and alcohols. The alcohol initiator can be any suitable alcohol, including mono-alcohol, diol, triol, or other polyol, with the proviso that the choice of alcohol does not adversely affect the polymerization yield, polymer molecular weight, complexation with a bio-active material, and/or the desirable mechanical and physical properties of the product polymer. The alcohol can also be multi-functional comprising, in addition to one or more hydroxyl groups, a halide, an ether group, an ester group, an amide group, or other functional group. Exemplary alcohols includes methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, poly(ethylene glycol), propylene glycol, alcohol functionalized block copolymers derived from oligomeric alcohols, or alcohol functionalized branched polymers derived from branched alcohols, or a combination thereof. In an embodiment, the ROP initiator is a monomeric diol selected from the group consisting of ethylene glycols, propylene glycols, hydroquinones, and resorcinols. Even more specifically, the initiator is BnMPA, a precursor used in the preparation of cyclic carbonate monomers:

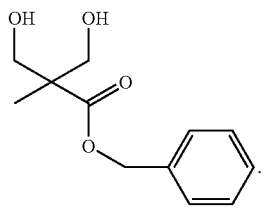

(BnMPA)

The ring-opening polymerization reaction can be performed with or without the use of a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable monomer concentration is about 0.1 to 5 moles per liter, and more particularly about 0.2 to 4 moles per liter. In a specific embodiment, reaction mixture for the ring-opening polymerization is free of a solvent.

The ring-opening polymerization can be performed at a temperature that is about ambient temperature or higher, more specifically a temperature from 15° C. to 200° C., and more particularly 20° C. to 200° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

Whether performed in solution or in bulk, the polymerizations are conducted in an inert (i.e., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

The catalyst is present in an amount of about 0.2 to 20 mol %, 0.5 to 10 mol %, 1 to 5 mol %, or 1 to 2.5 mol %, based on total moles of cyclic carbonyl monomer.

The nitrogen base accelerator is present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per hydroxyl group in the alcohol initiator. The hydroxyl groups are present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

In a specific embodiment, the catalyst is present in an amount of about 0.2 to 20 mol %, the nitrogen base accelerator is present in an amount of 0.1 to 5.0 mol %, and the hydroxyl groups of the initiator are present in an amount of 0.1 to 5.0 mol % based on the equivalent molecular weight per hydroxyl group in the initiator.

As stated above, the first polymer is a living polymer. The first polymer comprises a terminal hydroxyl group, terminal thiol group, or terminal amine group, each of which can initiate ROP chain growth. Herein, the first polymer is endcapped to prevent further chain growth and/or otherwise stabilize the backbone. Endcapping materials and techniques are well established in polymer chemistry. These include, for example materials for converting terminal hydroxyl groups to esters, such as carboxylic acid anhydrides, carboxylic acid chlorides, or reactive esters (e.g., p-nitrophenyl esters). In an embodiment, the first polymer is treated with acetic anhydride to endcap the chains with acetyl groups, forming the precursor polymer.

The first polymer and/or the precursor polymer can have a number average molecular weight $M_n$ as determined by size exclusion chromatography of at least 2500 g/mol, more specifically 4000 g/mol to 150000 g/mol, and even more specifically 10000 g/mol to 50000 g/mol. In an embodiment, the first polymer and/or the precursor polymer has a number average molecular weight $M_n$ of 10000 to 20000 g/mole. The first polymer and/or the precursor polymer also has a narrow polydispersity index (PDI), generally from 1.01 to 1.35, more particularly 1.10 to 1.30, and even more particularly 1.10 to 1.25. The first polymer and/or the precursor polymer can be a homopolymer, a random copolymer, or a block copolymer. In an embodiment, the cationic polymer is a polyester homopolymer, random polyester copolymer, a polycarbonate homopolymer, random polycarbonate copolymer, or a random polyestercarbonate copolymer.

The catalysts can be removed by selective precipitation or in the case of the solid supported catalysts, simply by filtration. The first polymer can comprise residual catalyst in an amount greater than 0 wt. % (weight percent), based on total weight of the first polymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the first polymer and the residual catalyst. Similarly, the precursor polymer can comprise a residual catalyst in an amount greater than 0 wt. %, based on total weight of the precursor polymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the precursor polymer and the residual catalyst.

The precursor polymer comprises first repeat units derived from the first cyclic carbonyl monomer. The first repeat units comprising a side chain moiety comprising a reactive monovalent leaving group, which when treated with a tertiary amine, produces a cationic polymer comprising a moiety comprising a quaternary amine. No limitation is placed on the structure of the tertiary amine, with the proviso that the tertiary amine is capable of reacting with more than 0%, 10% or more, 20% or more, 30% or more, 40% or more, 50% or more, 60% or more, 70% or more, or more particularly 80% or more of the monovalent leaving groups of the first repeat units to form a side chain moiety comprising a quaternary amine.

The tertiary amine can comprise a single nitrogen such as a trialkylamine, including but not limited to trimethylamine, triethylamine, tripropylamine, and the like. The tertiary amine can further comprise additional functional groups, in particular a carboxylic acid group, for example 3-(N,N-dimethylamino)propionic acid. In such instances, the cationic polymer will comprise first repeat units comprising a side chain moiety comprising a quaternary amine and a carboxylic acid group.

The tertiary amine can also comprise isotopically enriched versions of the tertiary amine, such as trimethylamine-$^{14}$C, trimethylamine-$^{15}$N, trimethylamine-$^{15}$N, trimethyl-$^{13}$C$_3$-amine, trimethyl-d$_9$-amine, and trimethyl-d$_9$-amine-$^{15}$N. The tertiary amine can also comprise a radioactive moiety suitable for targeting a specific cell type, such as a cancer cell. The radioactive moiety can comprise a heavy metal radioactive isotope.

More particularly, the tertiary amine is a bis-tertiary amine of the general formula (8):

where L" is a divalent linking group comprising 2 to 30 carbons, and each monovalent $R^b$ group is independently selected from alkyl groups comprising 1 to 30 carbons or aryl groups comprising 6 to 30 carbons. Each $R^b$ group can independently be branched or non-branched. Each $R^b$ group can independently comprise additional functional groups such as a ketone group, aldehyde group, hydroxyl group, alkene group, alkyne group, cycloaliphatic ring comprising 3 to 10 carbons, heterocylic ring comprising 2 to 10 carbons, ether group, amide group, ester group, and combinations of the foregoing additional functional groups. The heterocyclic ring can comprise oxygen, sulfur and/or nitrogen. Two or more $R^b$ groups can also together form a ring. Representative L" groups include —(CH$_2$)$_{z'}$— where z' is an integer from 2 to 30, —(CH$_2$CH$_2$O)$_{z''}$CH$_2$CH$_2$— where z" is an integer from 1 to 10, —CH$_2$CH$_2$SCH$_2$CH$_2$—, —CH$_2$CH$_2$SSCH$_2$CH$_2$—, —CH$_2$CH$_2$SOCH$_2$CH$_2$—, and —CH$_2$CH$_2$SO$_2$CH$_2$CH$_2$—. L" can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocylic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof.

More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3 propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In an embodiment, the bis-tertiary amine is TMEDA.

The precursor polymer is treated with the tertiary amine in a suitable organic solvent such as dimethylsulfoxide (DMSO) to form the cationic polymer. The reaction is conducted under anhydrous conditions, at ambient or elevated temperature using excess tertiary amine relative to the monovalent leaving group. In general, the tertiary amine is used in an amount of from 2 to 10 to moles per mole of monovalent leaving group in the precursor polymer, more particularly 3 to 8 moles per mole of monovalent leaving group in the precursor polymer, even more particularly 3 to 5 moles per mole of monovalent leaving group in the precursor polymer. The positive charged quaternary amine forms a salt with the displaced leaving group, which becomes a negatively charged counterion. Alternatively, the negatively charged counterion can be ion exchanged with another more suitable negatively charged counterion using known methods, if desired.

The cationic polymer is isolated by one or more precipitations in an organic solvent such as tetrahydrofuran, followed by filtration and drying in vacuo. More than 0% of the first repeat units comprise a side chain moiety comprising a quaternary amine group. When the precursor polymer is treated with a bis-tertiary amine, more than 0% of the first repeat units comprise a side chain moiety comprising a quaternary amine group and a tertiary amine group. When the precursor polymer is treated with a tertiary amine comprising a carboxy group, more than 0% of the first repeat units derived from the first cyclic carbonyl monomer comprise the side chain moiety comprising the quaternary amine and a carboxylic acid. The quaternary amine group is present in the cationic polymer in an amount of from more than 0% of the side chain monovalent leaving groups derived from the first cyclic carbonyl monomer. More particularly, the quaternary amine group is present in the cationic polymer in an amount of from 10 to 100%, 20 to 100%, 30 to 100%, 40 to 100%, 50 to 100%, 60 to 100%, 70 to 100%, or 80 to 100% of the side chain monovalent leaving groups derived from the first cyclic carbonyl monomer. When the precursor polymer is treated with a bis-tertiary amine, the tertiary amine group can be present in the cationic polymer in an amount of from more than 0% of the monovalent leaving groups in the first repeat units of the precursor polymer, more particularly from 10 to 100%, from 20 to 100%, from 30 to 100%, from 40 to 100%, from 50 to 100%, from 60 to 100%, from 70 to 100%, or from 80 to 100% of the monovalent leaving groups in the first repeat units of the precursor polymer.

The cationic polymer can have a number average molecular weight $M_n$ as determined by size exclusion chromatography of at least 2500 g/mol, more specifically 4000 g/mol to 150000 g/mol, and even more specifically 10000 g/mol to 50000 g/mol. In an embodiment, the cationic polymer has a number average molecular weight $M_n$ of 10000 to 20000 g/mole. The cationic polymer also has a narrow polydispersity index (PDI), generally from 1.01 to 1.35, more particularly 1.10 to 1.30, and even more particularly 1.10 to 1.25.

More particularly, the cationic polymer is an amphiphilic block copolymer comprising derived by sequential ring opening polymerization of a first cyclic carbonyl monomer and a second cyclic carbonyl monomer. The cationic polymer can comprises two or more block copolymer chains linked to the subunit derived from a polyol initiator. Each of the two or more block copolymer chains comprises a hydrophobic block and a hydrophilic block, and each of the two or more block copolymer chains can be optionally endcapped. In an embodiment, the cationic block copolymer comprises a hydrophilic core block comprising first repeat units derived from the first cyclic carbonyl monomer, wherein the first repeat units are linked to the subunit derived from a polyol initiator, and a hydrophobic outer block comprising second repeat units derived from a second cyclic carbonyl monomer. In another embodiment, the sequential polymerization of the cyclic carbonyl monomers is reversed. That is, the cationic block copolymer comprises a hydrophobic core block comprising second repeat units derived from the second cyclic carbonyl monomer, wherein the second repeat units are linked to the subunit derived from a polyol initiator, and a hydrophilic outer block comprising first repeat units derived from the first cyclic carbonyl monomer linked to the hydrophobic core block. In an embodiment, the polyol initiator is a monomeric diol.

In aqueous solution the cationic polymers self-assemble into nanoparticles having an average particle size, for example, of from 10 nm to 500 nm, 10 nm to 250 nm, 50 nm to 200 nm, 50 nm to 150 nm, 50 nm to 120 nm, and even more particularly from 50 nm to 100 nm, as measured by dynamic light scattering (Brookhaven Instrument Corp., Holtsville, N.Y., U.S.A.) equipped with a He—Ne laser beam at 658 nm (scattering angle: 90). The particle size measurements are repeated for 5 runs for each sample, and the particle size are reported as the average of 5 readings. For the foregoing particle sizes, the aqueous solution can have a pH of from 5.0 to 8.0.

A method of forming a biodegradable cationic polymer comprises forming a first mixture comprising a first cyclic carbonyl monomer, a catalyst, an accelerator, a monomeric diol initiator, and an optional solvent, wherein the first cyclic carbonyl monomer comprises a monovalent leaving group capable of reacting with a tertiary amine to form a quaternary amine; forming a first polymer comprising first repeat units derived from the first cyclic carbonyl monomer by ring-opening polymerization; optionally endcapping the first polymer to form a precursor polymer; and treating the precursor polymer with the tertiary amine to form the cationic polymer, wherein more than 0% of the repeat units derived from the first cyclic monomer comprise a side chain moiety comprising a quaternary amine. In an embodiment, the tertiary amine is a bis-tertiary amine and the side chain moiety comprises the quaternary amine and a tertiary amine. In another embodiment, the bis-tertiary amine is selected from the group consisting of N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3 propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In another embodiment, the tertiary amine comprises a carboxy group and the first repeat unit comprises a side chain moiety comprising the quaternary amine and a carboxylic acid. In another embodiment, the first mixture comprises a hydrophobic second cyclic carbonyl monomer, and the cationic polymer is a random copolymer comprising a second repeat unit derived from the second cyclic carbonyl monomer by ring-opening polymerization; wherein the second cyclic carbonyl monomer does not comprise a monovalent leaving group capable of reacting with a tertiary amine to form a quaternary amine. In another embodiment, the second repeat unit comprises a side chain acetal ester group.

Another method of forming a biodegradable cationic block copolymer comprises forming a reaction mixture comprising a catalyst, an accelerator, a monomeric diol initiator, and an optional solvent; sequentially adding to the reaction mixture and reacting by ring-opening polymerization a first cyclic carbonyl monomer followed by a second cyclic carbonyl monomer, thereby forming a first block copolymer, wherein the first cyclic carbonyl monomer comprises a monovalent leaving group capable of reacting with a tertiary amine to form a quaternaray amine, and the second cyclic carbonyl monomer is not capable of reacting with the tertiary amine to form the quaternary amine; optionally endcapping the first block copolymer, thereby forming a precursor block copolymer; and treating the precursor block copolymer with the tertiary amine to form the cationic polymer, wherein the cationic polymer comprises first repeat units derived from the first cyclic carbonyl monomer, and more than 0% of the first repeat units comprise a side chain moiety comprising the quaternary amine. In an embodiment, the sequential reaction is performed in reverse order to form the first block copolymer. In another embodiment, the first block copolymer is endcapped using a carboxylic anhydride, thereby forming a terminal ester group. In another embodiment, the cationic block copolymer comprises a second repeat unit derived from the second cyclic carbonyl monomer, and the second repeat unit comprises a side chain acetal ester group. In another embodiment, the initiator is a monomeric diol selected from the group consisting of ethylene glycols, propylene glycols, hydroquinones, and resorcinols. In another embodiment, the initiator is BnMPA. In another embodiment, the monovalent leaving group is selected from the group consisting of halides, sulphonate esters, and epoxides. In another embodiment, the tertiary amine is a bis-tertiary amine and the side chain moiety comprises the quaternary amine and a tertiary amine. In another embodiment, the bis-tertiary amine is selected from the group consisting of N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof.

In general, the cationic polymer obtained by ring-opening polymerization comprises as many branches as the number of initiating sites on the initiator. Further, the cationic polymer comprises as many blocks as the number of sequential ring-opening polymerizations prior to endcapping, with the understanding that successive ring-opening polymerizations are performed using different cyclic carbonyl monomer compositions.

The cationic polymers form complexes (polyplexes) with a negatively charged bio-active material such as a gene, a nucleotide, a protein, a peptide, a drug, or a combination thereof. In aqueous solution at a pH of from 5.0 to 8.0, the complexes self-assemble into nanoparticles having an average particle size, for example, of from 10 nm to 500 nm, 10 nm to 250 nm, 50 nm to 200 nm, 50 nm to 150 nm, 50 nm to 120 nm, and even more particularly from 50 nm to 100 nm, as measured by dynamic light scattering (Brookhaven Instrument Corp., Holtsville, N.Y., U.S.A.) equipped with a He—Ne laser beam at 658 nm (scattering angle: 90). The polymer/DNA complexes are prepared at various N/P ratios by gently mixing. Prior to particle size analysis, the complex solutions are allowed to stabilize for 30 minutes. The particle size measurements are repeated for 5 runs for each sample, and the particle size are reported as the average of 5 readings. In an embodiment, the bio-active material is a negatively charged genetic material, and the polyplex is tightly packed due to the strong interaction of oppositely charged groups on the cationic polymer and the negatively charged genetic material. The nano-sized complexes induce 0 to 15% hemolysis, more particularly no hemolysis, and have a cytotoxicity of 0 to 20%, or more particularly no cytotoxicity. In another embodiment, the bio-active material is a drug.

Also disclosed is a method of preparing a polymer complex for treating a cell, comprising contacting a first aqueous mixture comprising a biodegradable cationic polymer with a second aqueous mixture comprising a negatively charged biologically active material to form a third aqueous mixture comprising the polymer complex, wherein the biodegradable cationic polymer comprises: first repeat units derived from a first cyclic carbonyl monomer by ring-opening polymerization, a subunit derived from a monomeric diol initiator for the ring-opening polymerization, and an optional endcap group, wherein more than 0% of the first repeat units comprise a side chain moiety comprising a quaternary amine group. The polymer complex has a particle size of 50 to 500 nm at a pH of from 5.0 to 8.0.

Further disclosed is a method of treating a cell, comprising contacting the cell with a nanoparticles of a polymer complex comprising a biodegradable cationic polymer and a negatively charged biologically active material; wherein the biodegradable cationic polymer comprises: first repeat units derived from a first cyclic carbonyl monomer by ring-opening polymerization, a subunit derived from a monomeric diol initiator for the ring-opening polymerization, and an optional endcap group, wherein more than 0% of the first repeat units comprise a side chain moiety comprising a quaternary amine group. In an embodiment, the biodegradable polymer is an amphiphilic block copolymer. The nanoparticles can have a particle size of 50 to 500 nm at a pH of from 5.0 to 8.0. In an embodiment, the negatively charged biologically active material is a gene. The cells can be exposed to the polymer complex in vitro, ex vivo and then subsequently placed into an animal, or in vivo (for example, an animal or human). In another embodiment, the negatively charged biologically active material is a molecular drug or a protein. In another embodiment, the polymer complex induces no hemolysis. In another embodiment, the nanoparticles have no cytotoxicity.

Exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™ Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU111248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

Any cell that can be transfected by a non-viral vector can be treated with the above-described complexes. In particular the cells are eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described complexes can be used as non-viral transfection vectors. The target gene is not limited to any particular type of target gene or nucleotide sequence. For example, the target gene can be a cellular gene, an endogenous gene, an oncogene, a transgene, a viral gene, or translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

The following examples demonstrate that the biodegradable polycarbonate and poly(estercarbonate) copolymers produced by organocatalytic ring-opening polymerization are effective non-viral gene carriers. The combination of biodegradable halogen-containing carbonate and a simple quaternization reaction with amines provides a versatile pathway to forming cationic polymers for gene carriers having diverse functionality. The halide on the precursor polymers can be varied depending on the target architectures and the types of application. The precursor polymers, particularly those bearing chloride residues, form packed complexes with genes, and the polyplexes show low cytotoxicity. The cationic polycarbonates can self-assemble into micellar nanoparticles having a hydrophobic core and a positively charged surface. Therefore, they can also be used for delivery of small molecular drugs and proteins, and for simultaneous delivery of drugs and genes, or drugs and proteins.

EXAMPLES

Materials for Polymer Synthesis.

THF, DMF, and methylene chloride used in the reaction were obtained by a solvents drying system (Innovative). N-(3,5-trifluoromethyl)phenyl-N'-cyclohexyl-thiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, *Macromolecules,* 2006, 39 (23), 7863-7871, and dried by stirring in dry THF over CaH$_2$, filtering, and removing solvent under vacuum. BisMPA benzylester (BnMPA) was prepared as described below, and further dried by dissolving in dry THF, stirring with CaH$_2$, filtering, and removing the solvent in vacuo. Acetic anhydride, DMSO, N,N,N',N'-tetramethy-1,2-ethanediamine (TMEDA), 1,8-diazabicyclo[5,4,0]undec-7-ene (DBU), and (−)-sparteine were stirred over CaH$_2$, vacuum distilled, then stored over molecular sieves (3 Å). L-lactide and D-lactide (Purac, 99%) were recrystallized from dry toluene 3 times prior to use. Trimethylenecarbonate (TMC) was azeotropically dried from toluene prior to use. Other reagents were used as received.

Materials for Physicochemical and Biological Characterizations of Polymers.

Acetic acid, sodium acetate, polyethylenimine (PEI, branched, weight average molecular weight $M_w$, 25 kDa), agarose, ethidium bromide and 3-[4,5-dimethylthiazolyl-2]-2,5-diphenyl tetrazolium bromide (MTT) were all purchased from Sigma-Aldrich and used as received. Ultra pure water of HPLC grade was obtained from J. T. Baker (U.S.A.). Phosphate-buffered saline (PBS) and tris-boric acid-EDTA (TBE) buffers were purchased from 1st BASE (Malaysia) and diluted to the intended concentration before use. Reporter lysis buffer and luciferin substrate were purchased from Promega (U.S.A.). DMEM growth medium, fetal bovine serum (FBS), penicillin and streptomycin were all purchased from Invitrogen Corporation (U.S.A.). Plasmid DNA encoding the 6.4 kb firefly luciferase (pCMV-luciferase VR1255C) driven by cytomegalovirus (CMV) promoter was kindly provided by Car Wheeler, Vical (U.S.A.), which was amplified in *E. coli* DH5α and purified with Endofree Giga plasmid purification kit supplied by Qiagen (Dutch). HepG2 cell line was obtained from ATCC (U.S.A.) and grown under the recommended conditions according to the supplier.

Monomer Syntheses.

A particularly useful synthon for functional biodegradable monomers is so-called MTC family of cyclic carbonate monomer derived from 2,2-bis(methylol)propionic acid (bis-MPA). Bis-MPA provides a facile route to 5-methyl-5-carboxyl-1,3-dioxan-2-one (MTCOH) and derivative thereof, as shown in Scheme 1.

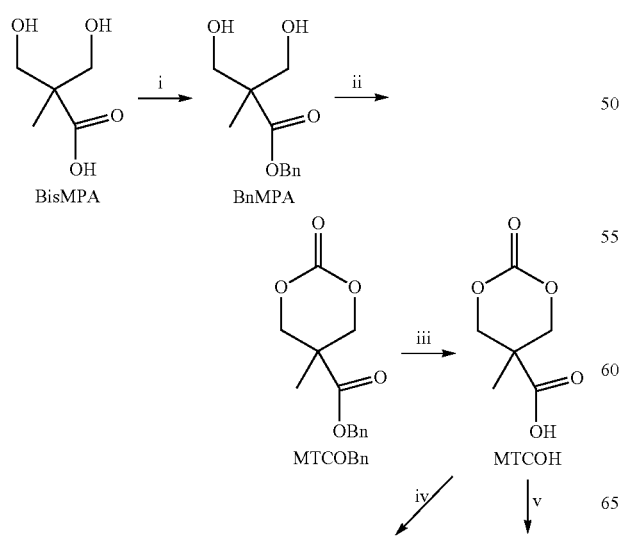

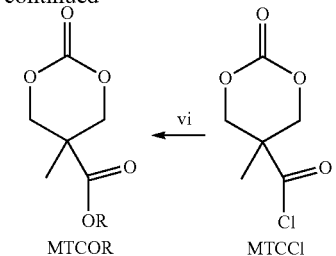

This approach parallels that of (meth)acrylate derivatization and has been demonstrated to create a wide selection of functional monomers capable of undergoing ring-opening polymerization. 2,2-Bis(methylol)propionic acid (BisMPA) is first converted (i) to a benzyl ester BnMPA (herein also used as an initiator for the polymerizations), followed by reaction (ii) of BnMPA with triphosgene to form a cyclic carbonyl monomer, MTCOBn. MTCOBn is debenzylated (iii) to produce the cyclic carbonyl carboxylic acid, MTCOH. Two pathways are shown for forming an ester from MTCOH. In the first pathway, (iv), MTCOH is treated with a suitable carboxy activating agent, such as dicyclohexylcarbodiimide (DCC), which reacts with ROH to form MTCOR in a single step. Alternatively, MTCOH can be converted first (v) to the acid chloride MTCCl followed by treatment (vi) of MTCCl with ROH in the presence of a base to form MTCOR. Both pathways are illustrative and are not meant to be limiting. The following conditions are typical for the reactions shown in Scheme 1: (i) Benzylbromide (BnBr), KOH, DMF, 100° C., 15 hours, 62% yield of the benzyl ester of bis-MPA; (ii) triphosgene, pyridine, CH$_2$Cl$_2$, 78° C. to 0° C., 95% yield of MTCOBn; (iii) Pd/C (10%), H2 (3 atm), EtOAc, room temperature, 24 hours, 99% yield of MTCOH; (iv) ROH, DCC, THF, room temperature, 1 to 24 hours; (v) (COCl)$_2$, THF, room temperature, 1 hour, 99% yield of MTCCl; (vi) ROH, NEt$_3$, RT, 3 hours yields MTCOR.

Using the above scheme, MTCCl was reacted with 3-bromopropanol, 3-choloropropano, 2-iodoethanol, and ethanol to form the corresponding MTCOPrBr, MTCOPrCl, MTCOEtI, and MTCOEt. The haloesters were purified by either recrystallization or by flash chromatography (ethyl acetate/hexane) in high yields (>85%). MTCOEt was used as a non-functional counterpart for dilution effects and to introduce hydrophobic blocks to the polymer for self-assembly.

Example 1. Preparation of 5-methyl-5-(3-chloropropyl)oxycarboxyl-1,3-dioxan-2-one, (MTCOPrCl), mw 236.65

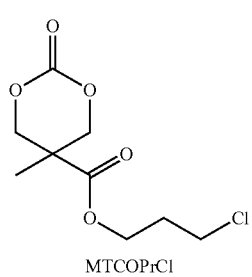

A catalytic amount (3 drops) of DMF was added to a THF solution (200 mL) of MTCOH (11.1 g, 69 mmol), followed by a solution of oxalyl chloride (7.3 mL, 87 mmol) in THF (100 mL), gently added over 20 min under $N_2$ atmosphere. The solution was stirred for 1 hour, bubbled with $N_2$ flow to remove volatiles, and evaporated under vacuum to give the intermediate.

A mixture of 3-chloro-1-propanol (5.4 mL, 76 mmol) and pyridine (6.2 mL, 65 mmol) in dry THF (50 mL) was added dropwise to a dry THF solution (100 mL) of the intermediate over 30 min, while maintaining a solution temperature below 0° C. with an ice/salt bath. The reaction mixture was kept stirring for another 3 hours at room temperature before it was filtered and the filtrate evaporated. The residue was dissolved in methylene chloride and washed with 1N HCl aqueous solution, saturated $NaHCO_3$ aqueous solution, brine and water, stirred with $MgSO_4$ overnight, and the solvent evaporated. The crude product was passed through a silica gel column by gradient eluting of ethyl acetate and hexane (50/50 to 80/20) to provide the product as a colorless oil that slowly solidified to a white solid (9.8 g, 60%).

Example 2. Preparation of 5-methyl-5-(3-bromopropyl)oxycarboxyl-1,3-dioxan-2-one, (MTCOPrBr), mw 281.10

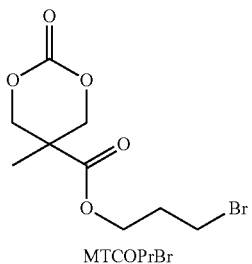

MTCOPrBr

MTCOPrBr was prepared by the procedure of Example 1 on a 45 mmol scale using 3-bromo-1-propanol as the alcohol. The product was purified by column chromatography, and subsequently recrystallized to yield white crystals (6.3 g, 49%). $^1$H NMR (400 MHz, $CDCl_3$): delta 4.69 (d, 2H; $CH_2OCOO$), 4.37 (t, 2H; $OCH_2$), 4.21 (d, 2H; $CH_2OCOO$), 3.45 (t, 2H; $CH_2Br$), 2.23 (m, 2H; $CH_2$), 1.33 (s, 3H; CH3). $^{13}$C NMR (100 MHz, $CDCl_3$): delta 171.0, 147.3, 72.9, 63.9, 40.2, 31.0, 28.9, 17.3.

Example 3. Preparation of 5-methyl-5-(2-iodoethyl)oxycarboxyl-1,3-dioxan-2-one, (MTCOEtI), mw 314.08

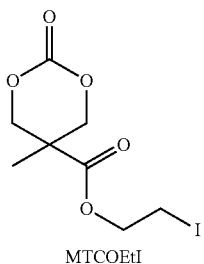

MTCOEtI

MTCOEtI was prepared by the procedure of Example 1 on a 45 mmol scale, using 2-iodoethanol as the alcohol, and was purified by column chromatography and subsequent recrystallization to yield yellowish crystals (7.7 g, 54%). $^1$H NMR (400 MHz, $CDCl_3$): delta 4.73 (d, 2H; $CH_2OCOO$), 4.45 (t, 2H; $OCH_2$), 4.22 (d, 2H; $CH_2OCOO$), 3.34 (t, 2H; $CH_2I$), 1.38 (s, 3H; $CH_3$). $^{13}$C NMR (100 MHz, $CDCl_3$): delta 170.5, 147.3, 72.8, 65.6, 40.3, 17.5, –0.3.

Organocatalytic Ring-Opening Polymerizations.

Ring-opening polymerizations were conducted using benzyl 2,2-bis(methylol)propionate (BnMPA) as an initiator in the presence of organocatalysts, N-(3,5-trifluoromethyl)phenyl-N'-cyclohexyl-thiourea (TU) and 1,8-diazabicyclo[5,4,0]undec-7-ene (DBU), in methylene chloride at room temperature (1-2 hours) to yield pre-cationic polymers comprising pendant 3-halopropyl esters with molecular weight consistent with the feed ratio ($[M]_0/[I]_0$), narrow polydispersities (1.1-1.2), and end group fidelity. To avoid scission of polymer chain by the back-biting stemming from the terminal hydroxyl group in the presence of amine during the reaction, the precursors were acetylated with acetic anhydride for 24 hours to 48 hours.

The ROP polymers prepared below have the general formula (9):

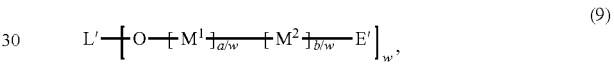

wherein L' is the subunit derived from the initiator, w is the number of initiating groups on L', $M^1$ is a cyclic carbonyl monomer, $M^2$ is a another cyclic monomer, E' is an endcap group, and a:b is the $M^1:M^2$ mole ratio. The initial ROP polymer is also referred to as a precursor polymer. In the preparation of block copolymers, is $M^1$ added first, followed by $M^2$. For random copolymers, it is understood that either monomer $M^1$ or $M^2$ can be attached to the initiator L'. Each polymerization was initiated with BnMPA, a diol; therefore w=2 and two polymer chains are formed that are linked by the subunit derived from the initiator. Each polymer chain was endcapped with acetyl groups using acetic anhydride.

Polycarbonates.

Example 5. Polymerization of MTCOPrCl

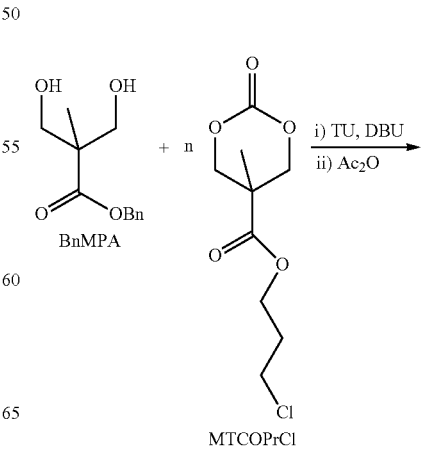

MTCOPrCl

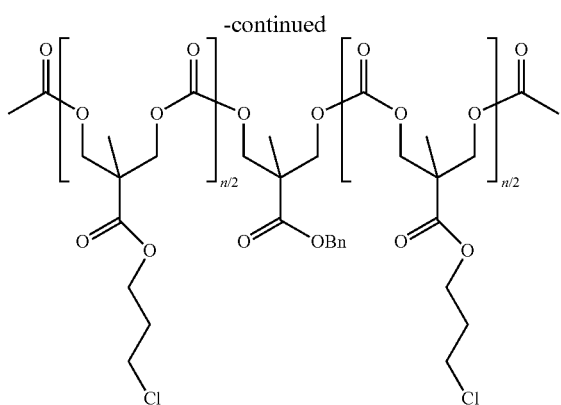

MTCOPrCl (501 mg, 2.1 mmol), BnMPA (4.7 mg, 0.02 mmol, initiator), and TU (37.2 mg, 0.1 mmol) were dissolved in methylene chloride (1 mL), and this solution was transferred to a vial containing DBU (15.2 mg, 0.1 mmol) to start polymerization at room, temperature ($[M]_0/[I]_0$=100). After 2 hours, acetic anhydride (72.4 mg, 0.71 mmol) was added into the mixture and the mixture was stirred for 48 hours (conversion ~95%). The solution was then precipitated into cold methanol twice and the precipitate was centrifuged and dried in vacuum. Yield: 466 mg (93%), GPC (THF): $M_n$ 12200 g/mol, PDI 1.17, $^1$H NMR (400 MHz, $CDCl_3$): delta 7.39-7.29 (m, 5H; Ph), 5.16 (s, 2H; $PhCH_2$), 4.38-4.19 (br, ~350H; $CH_2OCOO$, $OCH_2$ polymer), 3.64-3.55 (m, ~117H; $CH_2Cl$ polymer), 2.15-2.07 (m, ~114H; $CH_2$ polymer), 2.06 (s, 6H; $OCH_3$ acetyl end), 1.27 (br, ~169H; $CH_3$ polymer).

Example 6. Polymerization of MTCOPrBr

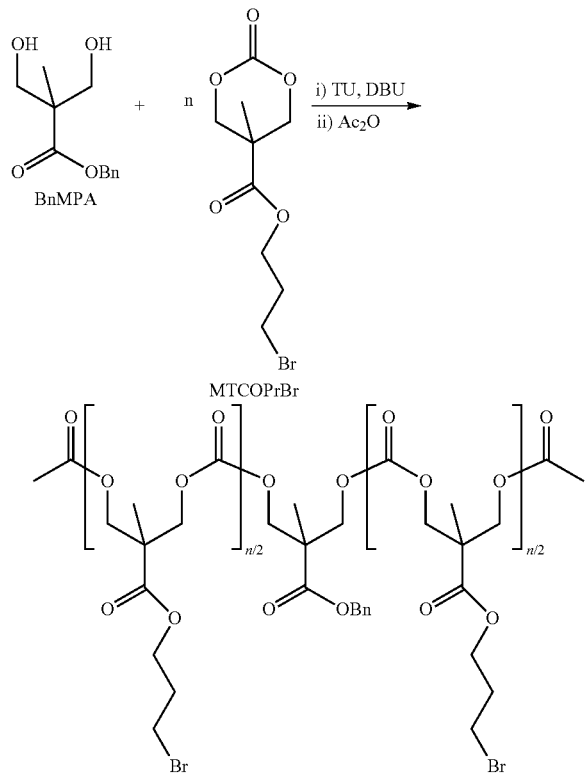

MTCOPrBr (288 mg, 1.0 mmol), BnMPA (4.4 mg, 0.01 mmol, initiator), and TU (9.8 mg, 0.03 mmol) were dissolved in methylene chloride (1 mL), and this solution was transferred to a vial containing DBU (3.3 mg, 0.02 mmol) to start polymerization at room, temperature ($[M]_0/[I]_0$=52). After 2 hours, acetic anhydride (96.9 mg, 0.95 mmol) was added into the mixture and stirred for 2 nights (conversion 94%). The solution was then precipitated into cold methanol twice and the precipitate was centrifuged and dried in vacuum. Yield: 265 mg (92%), GPC (THF): $M_n$ 11700 g/mol, PDI 1.11, $^1$H NMR (400 MHz, $CDCl_3$): delta 7.38-7.28 (m, 5H; Ph), 5.17 (s, 2H; $PhCH_2$), 4.40-4.17 (m, ~348H; $CH_2OCOO$, $OCH_2$ polymer), 3.53-3.36 (m, ~111H; $CH_2Br$ polymer), 2.23-2.15 (m, ~111H; $CH_2$ polymer), 2.06 (s, 6H; $OCH_3$ acetyl end), 1.30-1.24 (br, ~169H; $CH_3$ polymer).

Example 7. Polymerization of MTCOEtI

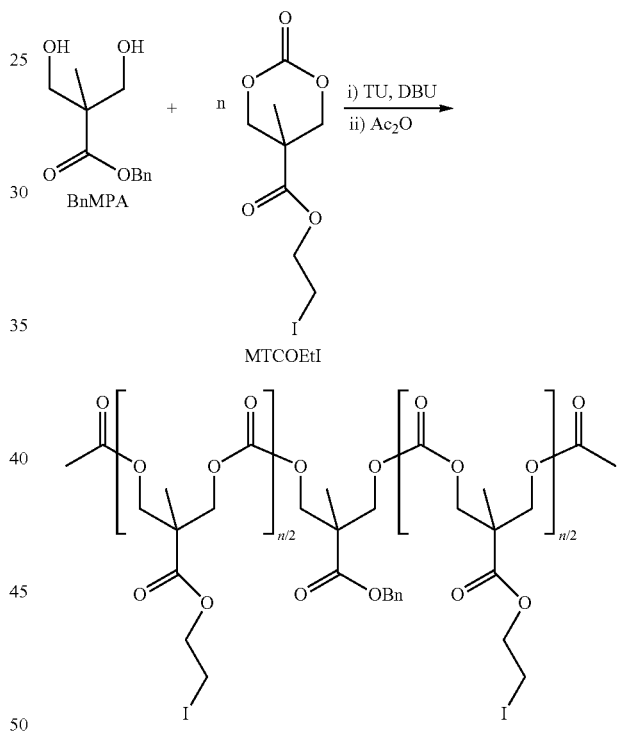

MTCOEtI (312 mg, 1.0 mmol), BnMPA (4.4 mg, 0.02 mmol, initiator), and TU (9.4 mg, 0.03 mmol) were dissolved in methylene chloride (1 mL), and this solution was transferred to a vial containing DBU (3.3 mg, 0.02 mmol) to start polymerization at room temperature ($[M]_0/[I]_0$=51). After 2 hours, acetic anhydride (107.2 mg, 1.05 mmol) was added into the mixture and stirred for 2 nights (conversion 94%). The solution was then precipitated into cold methanol twice and the precipitate was centrifuged and dried in vacuum. Yield: 268 mg (86%), GPC (THF): $M_n$ 10500 g/mol, PDI 1.22, $^1$H NMR (400 MHz, $CDCl_3$): delta 7.37-7.31 (m, 5H; Ph), 5.17 (s, 2H; $PhCH_2$), 4.44-4.36 (m, ~92H; $OCH_2$ polymer), 4.36-4.24 (m, ~178H; $CH_2OCOO$ polymer), 3.35-3.27 (m, ~89H; $CH_2I$ polymer), 2.07 (s, 6H; $OCH_3$ acetyl end), 1.34-1.24 (br, ~144H; $CH_3$ polymer).

Example 8. Block Polymerization of TMC and MTCOPrCl

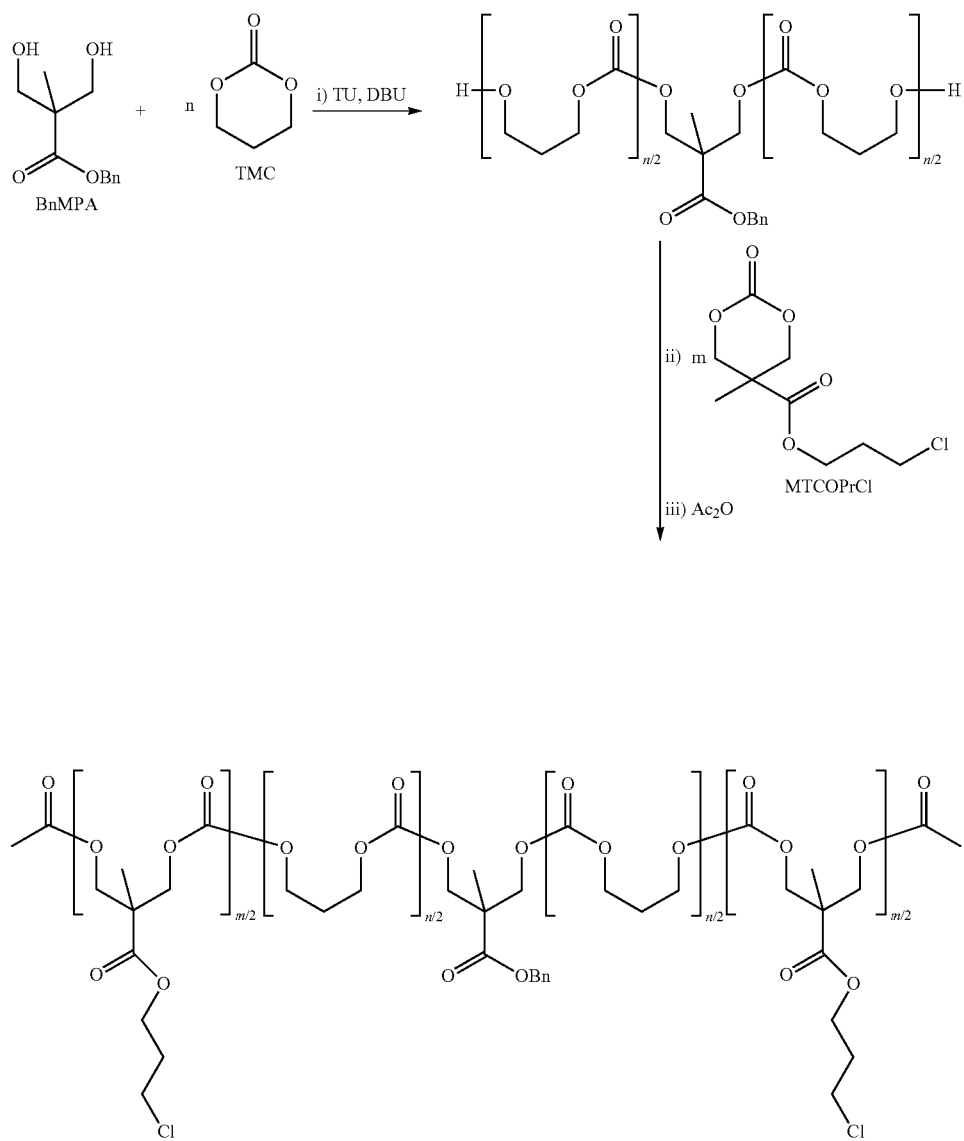

TMC (108 mg, 1.0 mmol, designated $M_1$), BnMPA (11 mg, 0.05 mmol), and TU (17.5 mg, 0.05 mmol) were dissolved in methylene chloride (1 mL), and this solution was transferred to a vial containing DBU (7.3 mg, 0.05 mmol) to start polymerization at room temperature ($[M_1]_0/[I]_0=20$). After complete consumption of the first monomer ($M_1$) was confirmed by NMR (3 hours, conversion 97%), the reaction mixture was transferred to a vial containing MTCO-PrCl (603 mg, 2.55 mmol), the second monomer $M_2$, for the second polymerization ($[M_2]_0/[I]_0=50$) and stirred for another 18 hours (conversion 96%). Acetic anhydride (117 mg, 1.15 mmol) was then added into the mixture and stirred for 2 nights. The solution was then precipitated into cold methanol twice and the precipitate was centrifuged and dried in vacuum. Yield: 640 mg (90%), GPC (THF): $M_n$ 12000 g/mol, PDI 1.19, $^1$H NMR (400 MHz, CDCl$_3$): delta 7.38-7.30 (m, 5H; Ph), 5.17 (s, 2H; PhCH$_2$), 4.33-4.26 (m, ~208H; CH$_2$OCOO, OCH$_{2\ P(MTCprCl)}$), 4.26-4.20 (m, ~70H, CH$_2$OCOO$_{PTMC}$), 3.63-3.56 (m, 73H; CH$_2$Cl$_{P(MTCprCl)}$), 2.15-2.00 (m, ~111H; CH$_2$ $_{P(MTCprCl)}$, CH$_2$ $_{PTMC}$, OCH$_3$ acetyl end), 1.27 (br, ~107H, CH$_3$ $_{P(MTCprCl)}$).

Polyester-Polycarbonate Block Copolymers.

Example 9. Block Polymerization of LLA and MTCOPrBr

In the following preparation, the stereochemistry of L-lactide (LLA) is not shown.

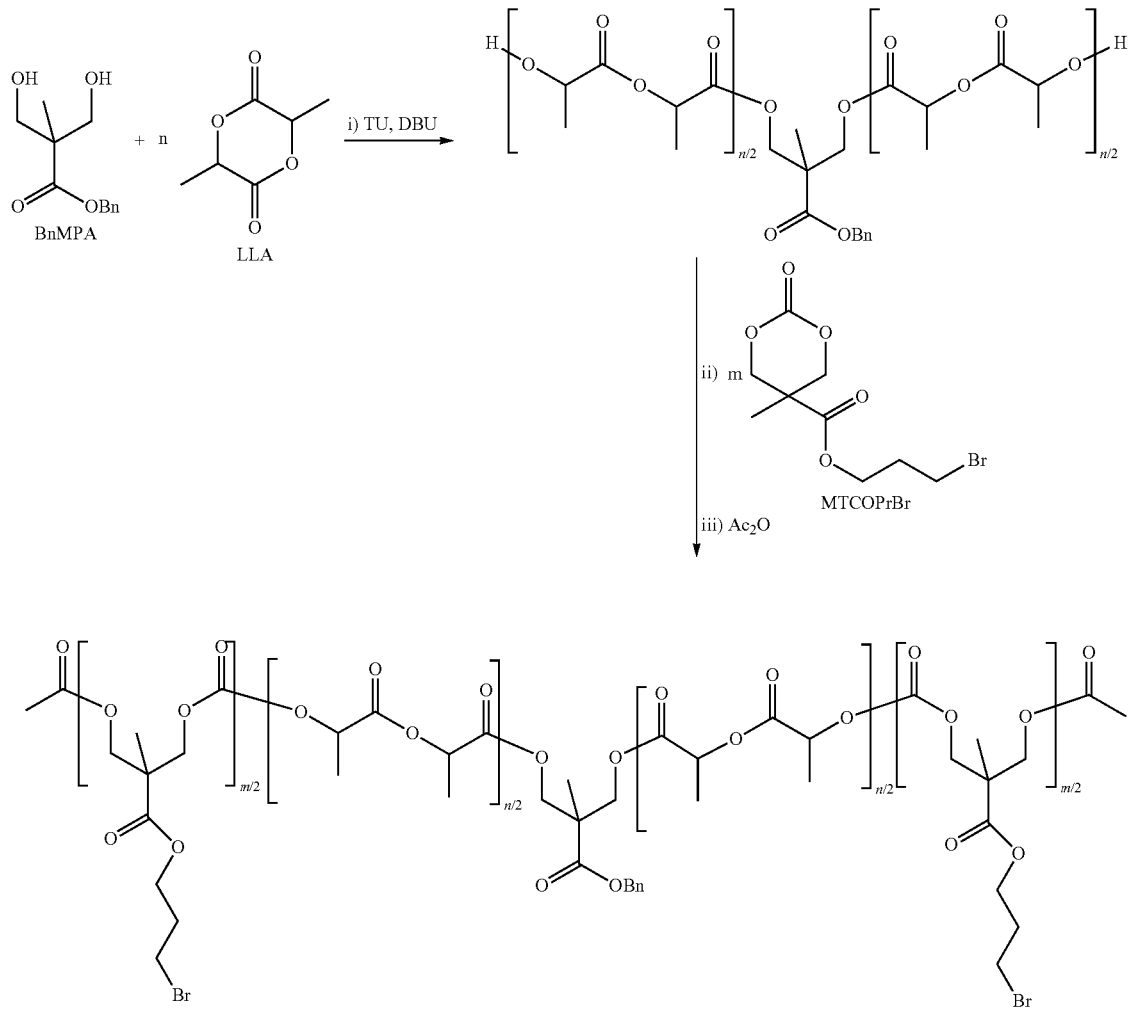

L-lactide (146 mg, 1.0 mmol) (LLA), BnMPA (12 mg, 0.05 mmol), and TU (9.0 mg, 0.024 mmol) were dissolved in methylene chloride (1 mL), and this solution was transferred to a vial containing (−)-sparteine (3.0 mg, 0.013 mmol) to start polymerization at room, temperature ($[M]_0/[I]_0$=20). After complete consumption of the first monomer was confirmed on NMR (1.5 h, conversion 96%), the reaction mixture containing the polyester was transferred to a vial containing MTCOPrBr (427 mg, 1.52 mmol), which was further transferred to a vial containing TU (9.7 mg, 0.026 mmol) and DBU (4.1 mg, 0.027 mmol) for the second polymerization ($[M_2]_0/[I]_0$=29). The second reaction mixture was stirred for another 1 hour (conversion 97%). Acetic anhydride (205 mg, 2.01 mmol) was then added into the mixture and stirred for 2 nights. The solution was then precipitated into cold methanol twice and the precipitate was centrifuged and dried in vacuum to provide the polyester-polycarbonate block copolymer. Yield: 524 mg (90%), GPC (THF): $M_n$ 12200 g/mol, PDI 1.14, $^1$H NMR (400 MHz, CDCl$_3$): delta 7.38-7.28 (m, 5H; Ph), 5.22-5.09 (m, ~35H; PhCH$_2$, CH$_{PLA}$), 4.38-4.19 (m, ~158H; CH$_2$OCOO, OCH$_2$ $_{P(MTCprBr)}$), 3.48-3.41 (m, ~56H, CH$_2$Br), 2.23-2.14 (m, ~55H; CH$_2$), 2.06 (s, 6H; OCH$_3$ acetyl end), 1.61-1.52 (m, ~106H; CH$_3$ $_{PLA}$), 1.32-1.27 (br, ~86H, CH$_3$ $_{P(MTCprBr)}$).

Example 10. Block Polymerization of DLA and MTCOPrBr

This polymer was prepared by the same procedure as Example 9, adding D-lactide (DLA) as the first monomer instead of L-lactide (LLA). Yield: 503 mg (87%), GPC (THF): $M_n$ 12400 g/mol, PDI 1.13. $^1$H NMR (400 MHz, CDCl$_3$): delta 7.38-7.28 (m, 5H; Ph), 5.22-5.09 (m, ~39H; PhCH$_2$, CH$_{PLA}$), 4.38-4.19 (m, ~195H; CH$_2$OCOO, OCH$_2$ $_{P(MTCprBr)}$), 3.48-3.41 (m, ~63H, CH$_2$Br), 2.23-2.14 (m, ~62H; CH$_2$), 2.06 (s, 6H; OCH$_3$ acetyl end), 1.61-1.52 (m, ~119H; CH$_3$ $_{PLA}$), 1.32-1.27 (br, ~97H, CH$_3$ $_{P(MTCprBr)}$)

Random Polycarbonate Copolymer.

Example 11. Random Polymerization of MTCOEt and MTCOPrBr

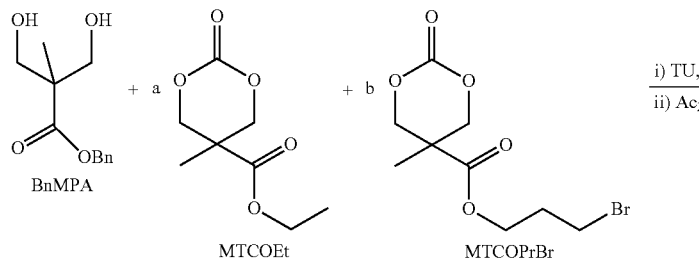

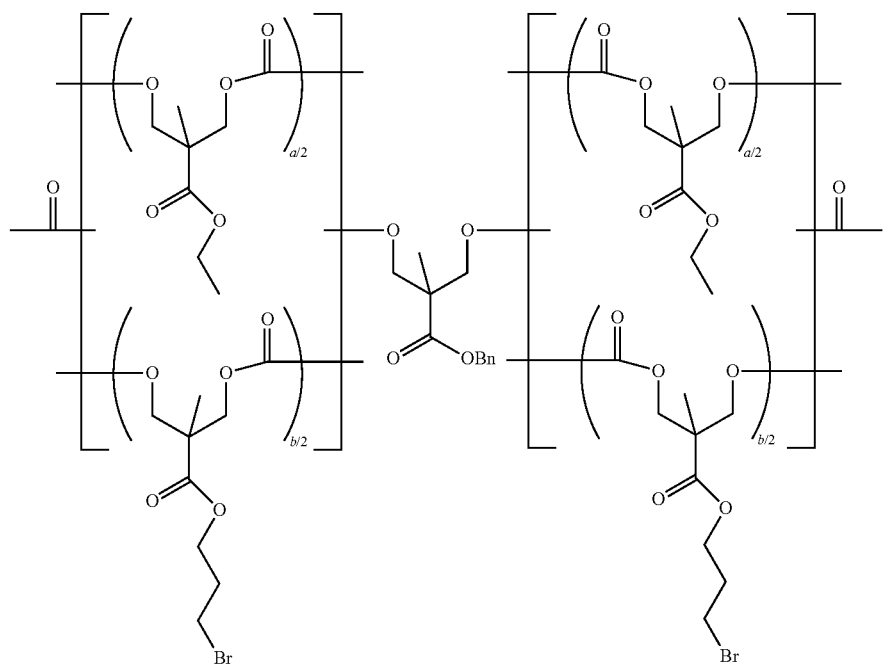

The vertical brackets in the above structure indicate that either of the repeat units derived from MTCOPrBr or MTCOEt can be bonded to the subunit derived from the initiator, as well as the acetyl group.

MTCOPrBr (282 mg, 1.0 mmol), MTCOEt (188 mg, 1.0 mmol), BnMPA (9.0 mg, 0.04 mmol), and TU (18.7 mg, 0.05 mmol) were dissolved in methylene chloride (1 mL), and this solution was transferred to a vial containing DBU (7.8 mg, 0.05 mmol) to start polymerization at room, temperature ($[M]_0/[I]_0$=50). After 2 hours, acetic anhydride (194 mg, 1.90 mmol) was added into the mixture and stirred for 2 nights (conversion 93%). The solution was then precipitated into cold methanol twice and the precipitate was centrifuged and dried in vacuum. Yield: 370 mg (77%), GPC (THF): $M_n$ 11400 g/mol, PDI 1.20, $^1$H NMR (400 MHz, CDCl$_3$): delta 7.37-7.31 (m, 5H; Ph), 5.16 (s, 2H; PhCH$_2$), 4.35-4.24 (m, ~247H; CH$_2$OCOO, OCH$_2$ $_{PMTC(prBr)}$), 4.23-4.14 (m, ~56H; OCH$_2$ $_{PMTC(Et)}$), 3.48-3.41 (m, ~47H; CH$_2$Br), 2.23-2.14 (m, ~47H; CH$_2$ $_{PMTC(prBr)}$), 2.06 (s, 6H; OCH$_3$ acetyl end), 1.30-1.20 (m, ~227H; CH$_3$, CH$_2$CH$_3$ $_{PMTC(Et)}$).

Preparation of Cationic Polymers.

The pre-cationic halo-functional polymers (i.e., initial ROP polymers) were reacted with N,N,N',N'-tetramethyl-ethylenediamine (TMEDA) in DMSO to provide the corresponding cationic polymers. Several bis-amines were surveyed, but only tertiary amines were chosen as feasible reagents because the primary and secondary amines led to a significant reduction in the polycarbonate backbone.

Example 12

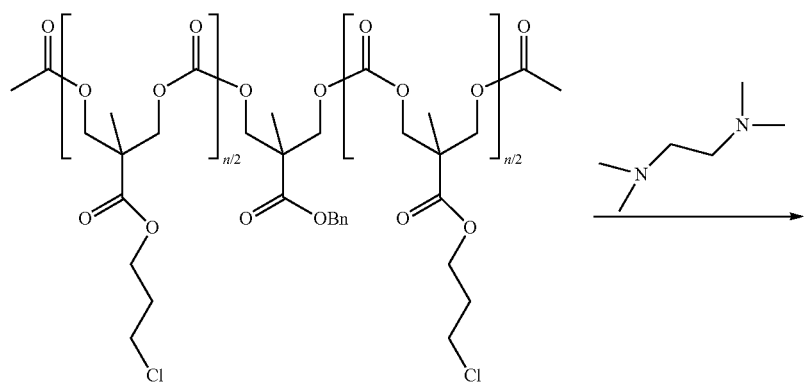

The homopolymer of Example 5 (427 mg, [Cl]=1.77 mmol) was dissolved in DMSO (8 mL) and mixed with TMEDA (1.1 mL, 7.22 mmol), and stirred for 6 h at 90° C. The mixture was then precipitated into THF twice and the precipitate was collected by centrifugation and dried in vacuum. Yield: 546 mg (86%), GPC (DMF): $M_n$ 11300 g/mol, PDI 1.27, $^1$H NMR (400 MHz, MeOH-$d_4$): delta 7.42-7.32 (br, 5H; Ph), 5.19 (s, 2H; PhCH$_2$), 4.45-4.17 (m, ~252H; CH$_2$OCOO, OCH$_2$ polymer), 3.63-3.44 (br, 149H; CH$_2$N$^+$ polymer), 3.27-3.18 (br, ~210H; N$^+$CH$_3$ polymer), 2.85-2.76 (br, 73H; CH$_2$N polymer), 2.36-2.30 (br, ~213H; NCH$_3$ polymer), 2.28-2.17 (br, ~70H; CH$_2$ polymer), 2.06 (s, 3H; OCH$_3$ acetyl end), 1.34-1.25 (br, ~119H; CH$_3$ polymer), 1.22 (s, 3H; CH$_3$ end group).

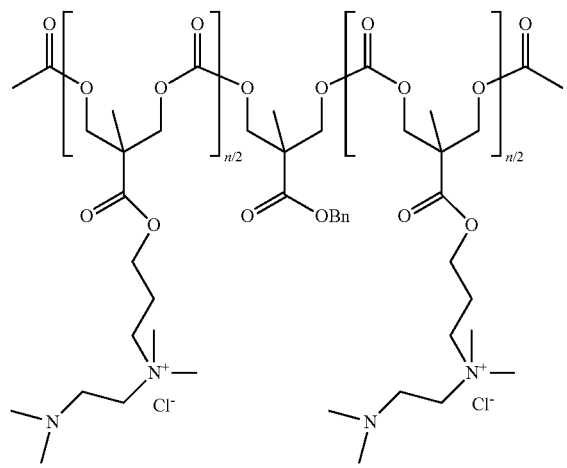

Example 13

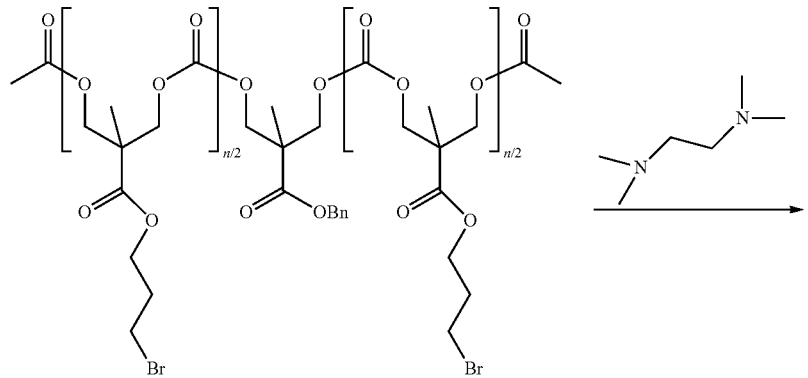

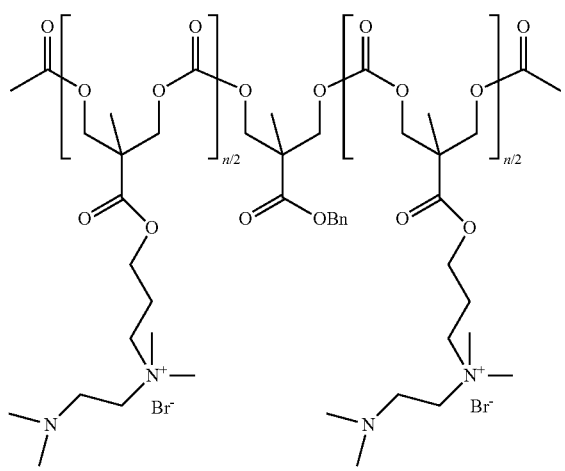

TMEDA (0.38 mL, 2.5 mmol) was added to a DMSO solution (3 mL) of the polymer formed in Example 6 (177 mg, [Br]=0.62 mmol). The solution was stirred overnight at room temperature and precipitated into THF twice, and the precipitate was centrifuged and dried in vacuum. Yield: 220 mg (88%), $^1$H NMR (400 MHz, MeOH-$d_4$): delta 7.42-7.30 (br, 5H; Ph), 5.20 (s, 2H; PhCH$_2$), 4.46-4.13 (m, ~266H, CH$_2$OCOO, OCH$_2$ polymer), 3.66-3.42 (br, ~168H; CH$_2$N$^+$ polymer), 3.28-3.17 (br, ~243H; N$^+$CH$_3$ polymer), 2.87-2.75 (br, ~84H; NCH$_2$ polymer), 2.37-2.29 (br, ~251H; NCH$_3$ polymer), 2.30-2.16 (br, ~85H; CH$_2$ polymer), 2.07 (s, 6H; OCH$_3$ acetyl end), 1.37-1.23 (br, ~133H; CH$_3$ polymer).

Example 14

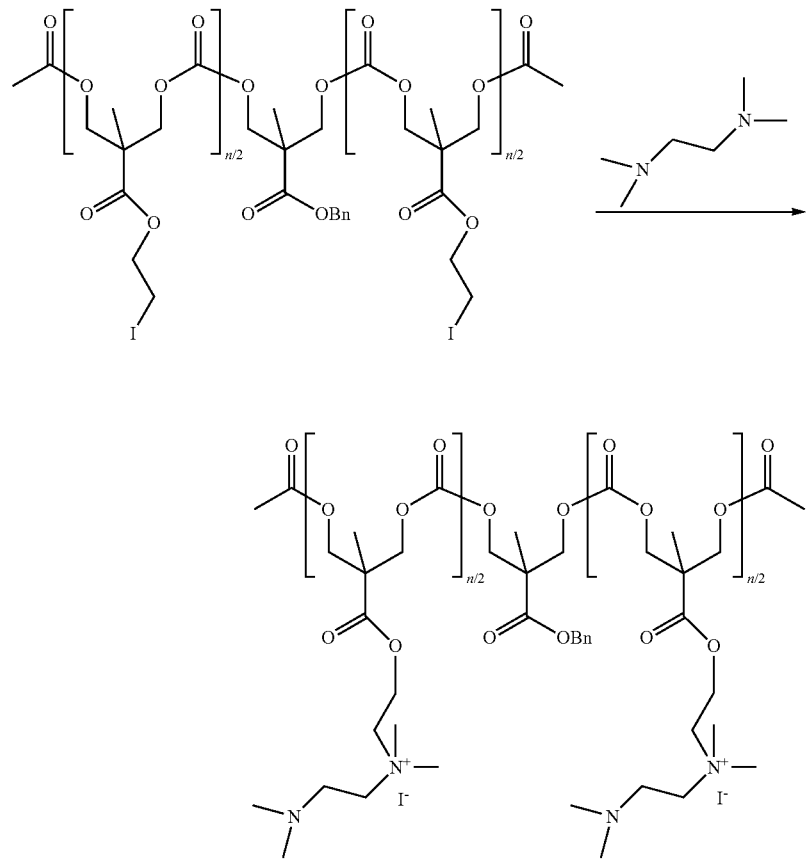

This cationic polymer was prepared using the same procedure described in Example 13 except with the polymer prepared in Example 7, on a 201 mg scale. Yield: 211 mg (77%), ¹H NMR (400 MHz, D$_2$O): delta 7.49-7.31 (m, 5H; Ph), 5.22 (s, 2H; PhCH$_2$), 4.69-4.56 (br, ~68H; OCH$_2$), 4.47-4.23 (m, ~176H; OCOCH$_2$), 3.90-3.76 (br, ~74H; N$^+$CH$_2$), 3.66-3.51, (br, ~78H; OCH$_2$CH$_2$N$^+$), 3.29-3.15 (br, ~220H; N$^+$CH$_3$), 2.93-2.82 (br, ~76H; NCH$_2$), 2.33-2.23 (br, ~222H; NCH$_3$), 2.07 (s, 6H; CH$_3$ acetyl), 1.38-1.20 (br, ~124H; CH$_3$).

Example 15

To a DMSO solution (10 mL) of the polymer formed in Example 8 (578 mg, [Cl]=1.93 mmol), TMEDA (1.27 mL, 8.5 mmol) was added. The reaction mixture was stirred for 6 h at 90° C. and precipitated into THF twice. The precipitate was centrifuged and dried into vacuum. Yield: 735 mg (92%), GPC (DMF): M$_n$ 15700 g/mol, PDI 1.27, ¹H NMR (400 MHz, MeOH-d$_4$): delta 7.41-7.32 (br, 5H; Ph), 5.19 (br, 2H; PhCH$_2$), 4.48-4.13 (br, ~388H; CH$_2$OCOO, OCH$_2$ polymer), 3.65-3.45 (br, ~179H; CH$_2$N$^+$ polymer), 3.28-3.18 (br, ~270H; N$^+$CH$_3$ polymer), 2.87-2.77 (br, ~88H; NCH$_2$ polymer), 2.38-2.30 (br, 272H; NCH$_3$ polymer), 2.28-2.16 (br, ~88H; CH$_2$ polymer), 2.08-1.98 (m, ~44H; CH$_2$ polymer, OCH$_3$ acetyl end), 1.35-1.25 (br, ~149H; CH$_3$ polymer).

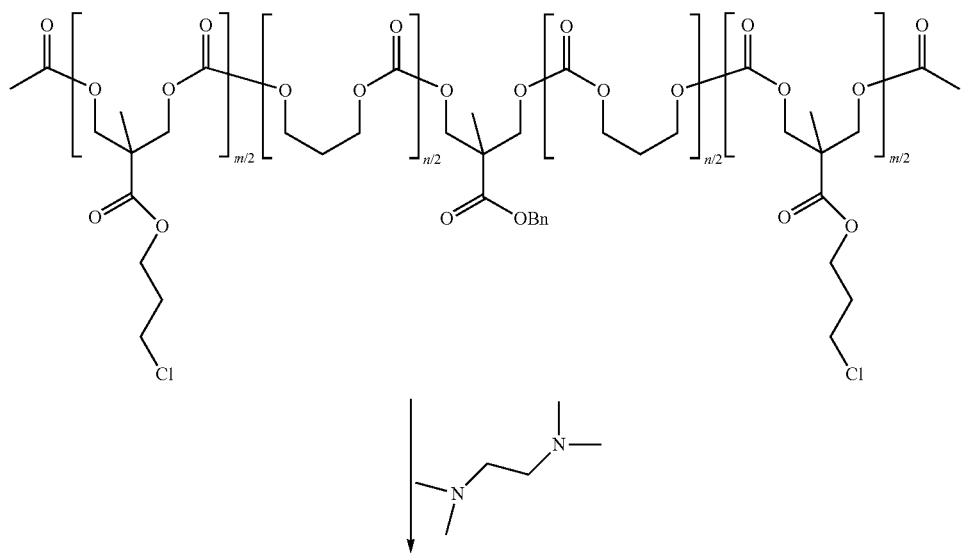

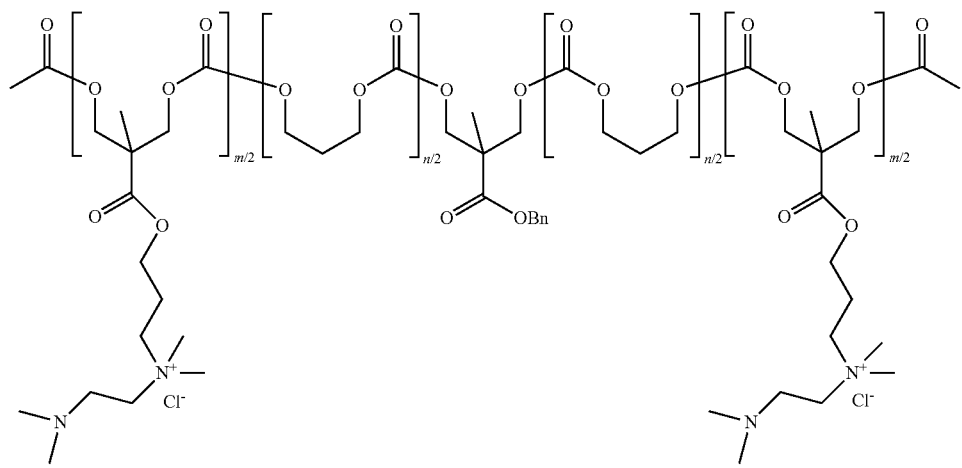

Example 16

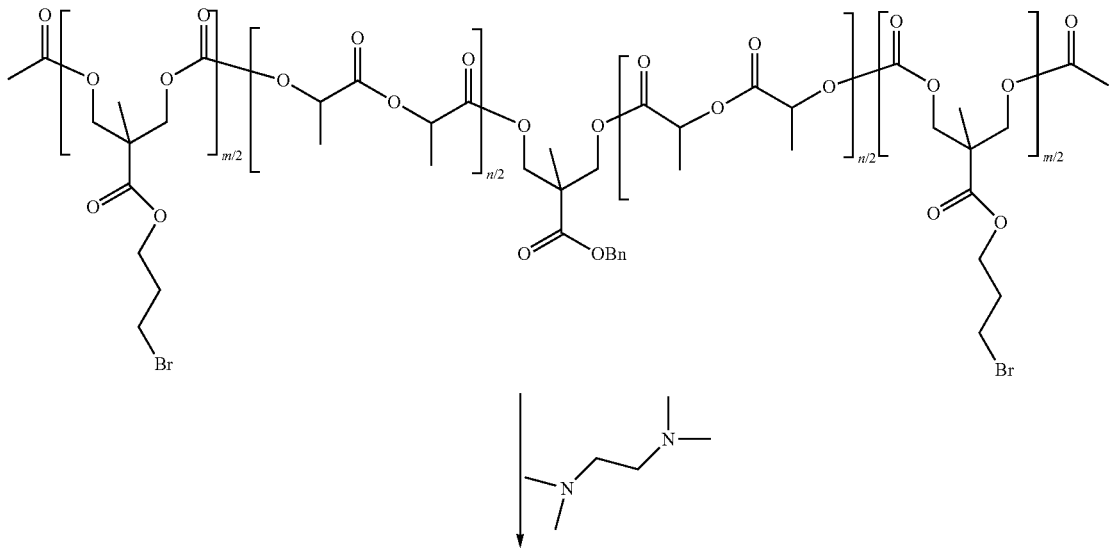

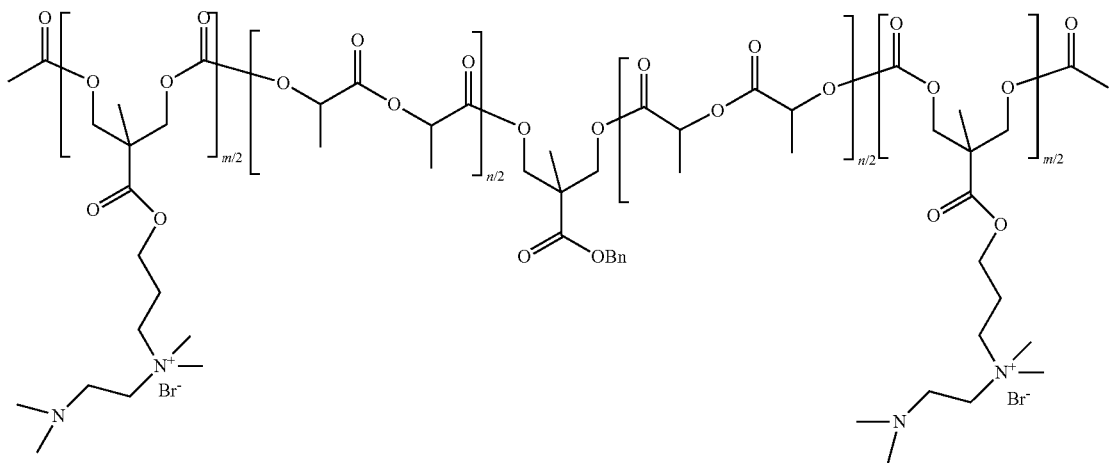

The polymer formed in Example 9 (406 mg, [Br]=1.07 mmol) and TMEDA (0.65 mL, 4.3 mmol) were mixed in DMSO (4.0 mL), stirred overnight at room temperature and precipitated into THF twice. The precipitate was centrifuged and dried into vacuum. Yield: 515 mg (97%), $^1$H NMR (400 MHz, MeOH-$d_4$): delta 7.42-7.30 (br, 5H; Ph initiator), 5.29-5.11 (m, ~42H; PhCH$_2$ initiator, CH$_{PLA}$), 4.49-4.15 (br, ~204H, CH$_2$OCOO, OCH$_2$ polymer), 3.67-3.43 (br, ~123H, CH$_2$N$^+$ polymer), 3.29-3.15 (br, ~177H, N$^+$CH$_3$ polymer), 2.85-2.74 (br, ~61H, NCH$_2$ polymer), 2.37-2.28 (br, ~189H, NCH$_3$ polymer), 2.29-2.15 (br, ~62H, CH$_2$ polymer), 2.06 (s, 6H, OCH$_3$ acetyl end), 1.60-1.50 (m, ~128H; CH$_3$ $_{PLA}$), 1.35-1.24 (br, ~103H, CH$_3$).

Example 17

This polymer from Example 10 was treated with TMEDA according to the procedure used in Example 16 to obtain a cationic polymer, the difference being the subunit derived from DLA rather than LLA. Yield: 497 mg (96%), $^1$H NMR (400 MHz, MeOH-$d_4$): delta 7.42-7.31 (br, 5H; Ph initiator), 5.24-5.13 (m, ~41H; PhCH$_2$ initiator, CH$_{PLA}$), 4.46-4.18 (m, ~206H, CH$_2$OCOO, OCH$_2$ polymer), 3.66-3.45 (br, ~124H, CH$_2$N$^+$ polymer), 3.28-3.18 (br, ~173H, N$^+$CH$_3$ polymer), 2.84-2.75 (br, ~57H, NCH$_2$ polymer), 2.35-2.28 (br, ~175H, NCH$_3$ polymer), 2.28-2.16 (br, ~59H, CH$_2$ polymer), 2.06 (s, 6H, OCH$_3$ acetyl end), 1.59-1.52 (m, ~121H; CH$_3$ $_{PLA}$), 1.35-1.25 (br, ~110H, CH$_3$).

Example 18
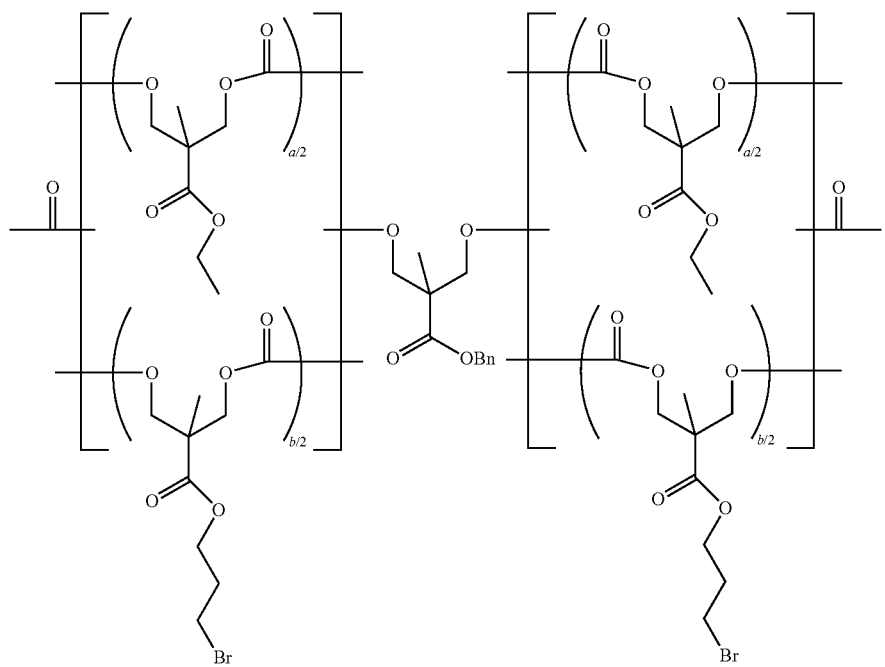
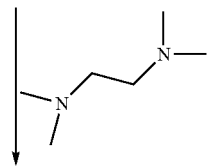
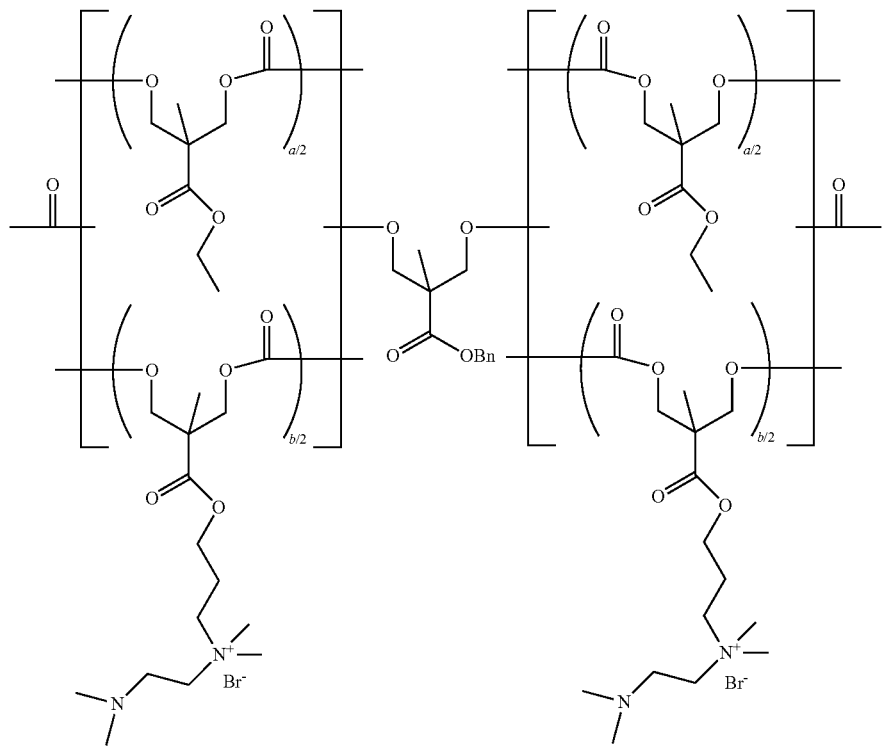

TMEDA (0.40 mL, 2.69 mmol) was added to a DMSO solution (3 mL) of the polymer from Example 11 (342 mg, [Br]=0.67 mmol). The solution was stirred overnight at room temperature and precipitated into the mixture of THF/hexane (3:1) twice, and the precipitate was centrifuged and dried in vacuum. Yield: 377 mg (90%), $^1$H NMR (400 MHz, MeOH-d$_4$): delta 7.41-7.35 (br, 5H; Ph), 5.19 (s, 2H; PhCH$_2$), 4.42-4.23 (m, ~253H, CH$_2$OCOO, OCH$_2$ $_{PMTC(prBr-N)}$), 4.28-4.13 (m, ~56H; OCH$_2$ $_{PMTC(Et)}$), 3.64-3.49 (br, ~96H; CH$_2$N$^+$), 3.28-3.19 (br, ~142H; N$^+$CH$_3$), 2.84-2.75 (br, ~52H; NCH$_2$), 2.35-2.28 (br, ~145H; NCH$_3$), 2.29-2.17 (br, ~49H; CH$_2$ $_{PMTC(prBr-N)}$), 2.06 (s, 6H; OCH$_3$ acetyl end), 1.35-1.19 (m, ~234H; CH$_3$ polymer).

Charge Shifting Polymers.

Example 19

5-methyl-5-(1-ethoxyethyl)oxycarboxyl-1,3-dioxan-2-one (MTCOEE; 62 mg, 0.27 mmol), MTCOPrBr (212 mg, 0.75 mmol), BnMPA (4.6 mg, 0.02 mmol), and TU (19.4 mg, 0.05 mmol) were dissolved in methylene chloride (1 mL), and this solution was transferred to a vial containing DBU (7.4 mg, 0.05 mmol) to start polymerization at room, temperature ([M]$_0$/[I]$_0$=50). After 2.5 h, the solution was precipitated into cold methanol and the precipitate was centrifuged and dried in vacuum. Yield: 241 mg (87%), GPC (THF): M$_n$ 11800 g/mol, PDI 1.19, $^1$H NMR (400 MHz, acetone-d$_6$): delta 7.45-7.32 (m, 5H; Ph), 5.96 (q, ~12H; CH$_{(OEE)}$), 5.20 (s, 2H; PhCH$_2$), 4.42-4.22 (m, ~333H; CH$_2$OCOO, OCH$_2$ $_{polymer}$), 3.75-3.48 (m, ~128H; OCH$_2$ $_{(OEE)}$, CH$_2$Br), 2.27-2.16 (m, ~87H; CH$_2$ $_{(OPrBr)}$), 1.35 (d, ~44H; CHCH$_3$ $_{(OEE)}$), 1.33-1.23 (m, ~182H; CH$_3$ $_{polymer}$), 1.22-1.08 (m, ~69H; CH$_3$ $_{(OEE)}$). a:b=1.0:3.1.

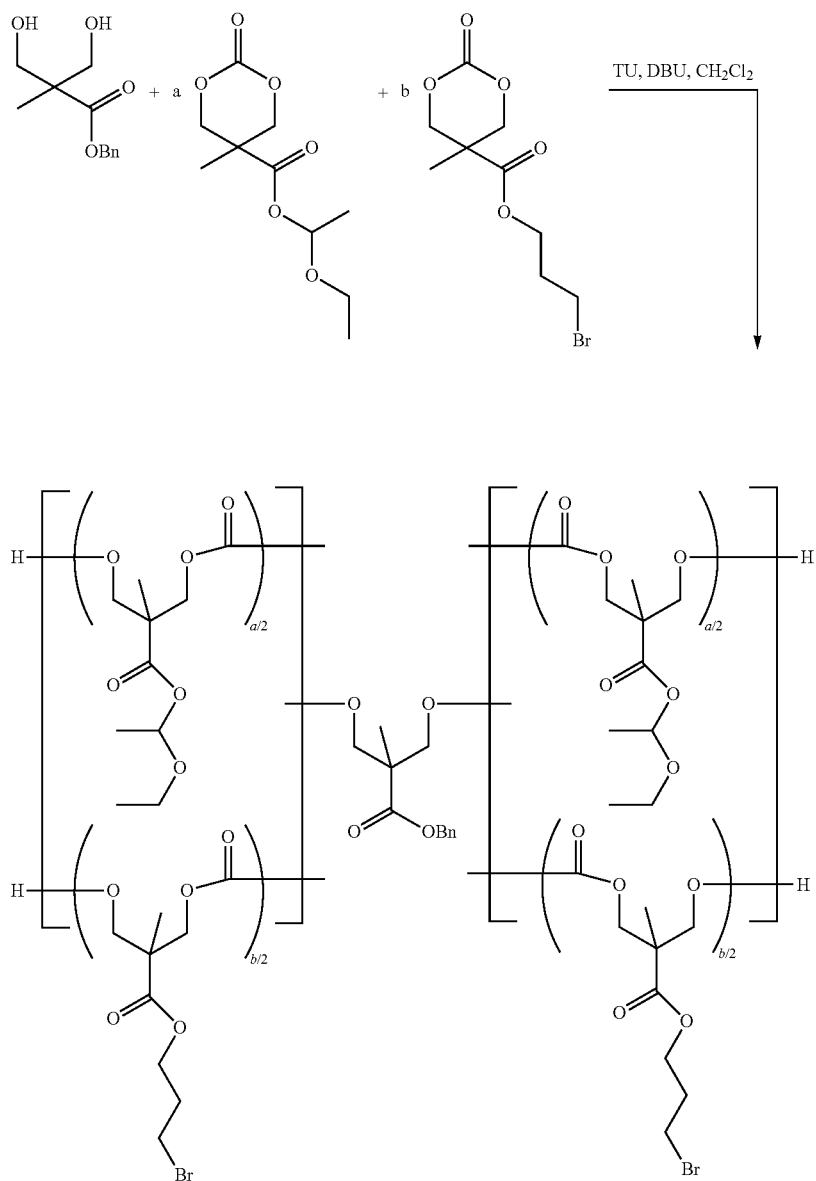

Example 20. Quaternization of Example 19
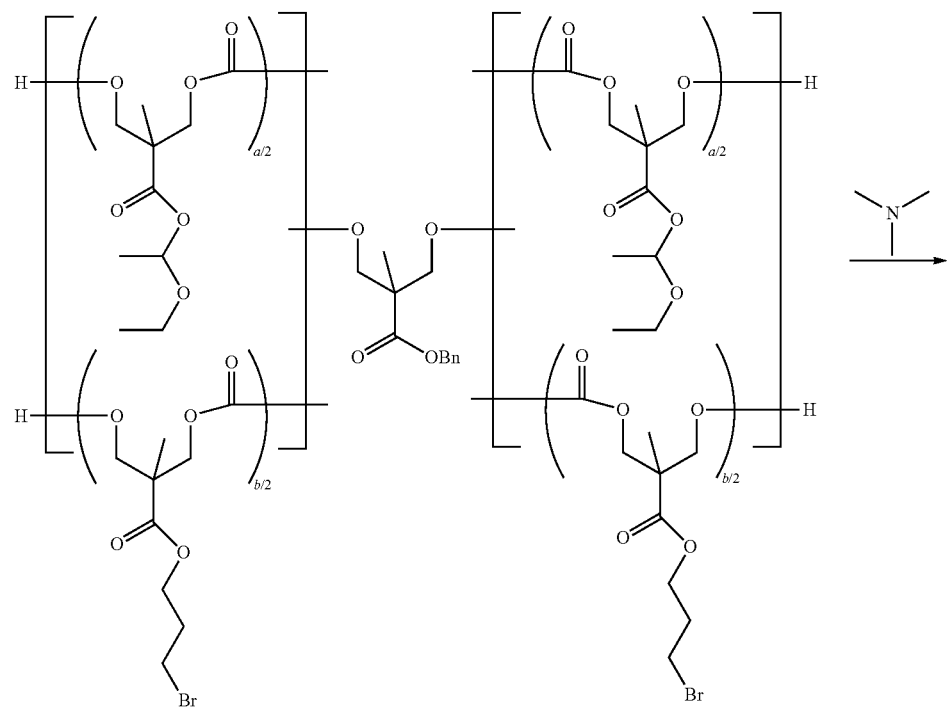
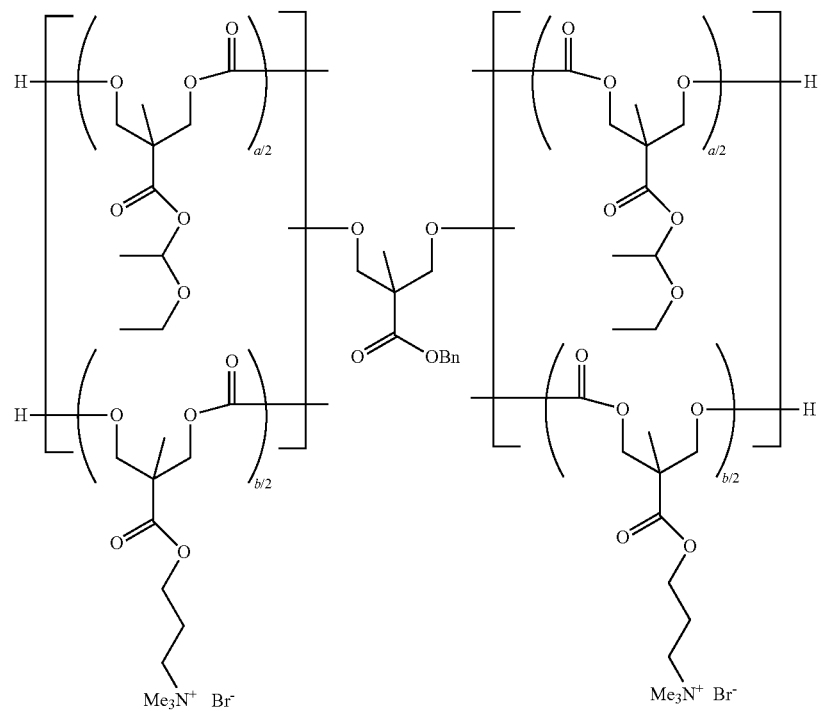

Trimethylamine gas (394 mg, 6.7 mmol) was charged to an acetonitrile solution (4 mL) of the polymer of Example 19 (202 mg, [Br]=0.56 mmol) immersed in a dry-ice/acetone bath. The solution was then allowed to warm to room temperature and kept stirring for 18 h before acetonitrile and excess gasses were removed under vacuum. The concentrated residue was dried in vacuum (~90% aminated). Yield: 200 mg (85%), $^1$H NMR (400 MHz, MeOH-d$_4$): delta 7.43-7.32 (m, 5H; Ph), 6.02-5.93 (m, ~6H; $CH_{(OEE)}$), 5.21 (s, 2H; $PhCH_2$), 4.48-4.11 (m, ~267H; $CH_2OCOO$ and $CH_2O_{polymer}$), 3.75-3.64 (m, ~15H; $OCH_2CH_{3\ (OEE)}$), 3.63-3.45 (m, ~78H; $N^+CH_2$ (PAB)), 2.29-2.15 (b, ~298H; $N^+CH_{3\ (PAB)}$), 2.32-2.15 (b, ~68H; $CH_{2\ (PAB)}$), 1.41-1.35 (d, ~19H; $CHCH_{3\ (OEE)}$), 1.35-1.23 (m, ~122H; $CH_{3\ polymer}$), 1.24-1.10 (m, ~46H; $CH_2CH_{3\ (OEE)}$). $M_n$ (NMR)=14700 g/mol.

The polymer preparations are summarized in Table 8 for precursor polymers (Examples 5 to 11, and 19) and their corresponding cationic polymers (Examples 12 to 18, and 20)

TABLE 8

| | Precursor Polymer[a,b] | | | |
|---|---|---|---|---|
| Example | Random/Block | M$^1$ | M$^2$ | Cationic Polymer[c] Example |
| 5 | | MTCOPrCl | | 12 |
| 6 | | MTCOPrBr | | 13 |
| 7 | | MTCOEtI | | 14 |
| 8 | Block | TMC | MTCOPrCl | 15 |
| 9 | Block | LLA | MTCOPrBr | 16 |
| 10 | Block | DLA | MTCOPrBr | 17 |
| 11 | Random | MTCOEt | MTCOPrBr | 18 |
| 19 | Random | MTCOEE | MTCOPrBr | 20 |

[a]Each polymerization was initiated with BnMPA.
[b]M$^1$ was added first for block copolymerizations.
[c]Quaternizations were performed with TMEDA.

Table 9 summarizes the analytical data (number average molecular weight $M_n$, polydispersity index (PDI), % yield, % conversion of the halide X to quaternary amine) obtained on the precursor polymers (Examples 5 to 11, and 19) and their corresponding cationic polymers (Examples 12 to 18, and 20).

TABLE 9

| Initial ROP Polymer | | | | Cationic Polymer | | | | |
|---|---|---|---|---|---|---|---|---|
| Example | $M_n$[a] | PDI[a] | Yield (%) | Example | $M_n$[b] | Yield (%) | $N^{+b,c}$ (%) | X |
| 5 | 12200 | 1.17 | 93 | 12 | 13900 | 86 | 85 | Cl |
| 6 | 11700 | 1.11 | 92 | 13 | 17500 | 88 | 93 | Br |
| 7 | 10500 | 1.22 | 86 | 14 | 17400 | 77 | 90 | I |
| 8 | 12000 | 1.19 | 90 | 15 | 18100 | 92 | 91 | Cl |
| 9 | 12200 | 1.14 | 90 | 16 | 16500 | 97 | 90 | Br |
| 10 | 12400 | 1.13 | 87 | 17 | 16100 | 96 | 85 | Br |
| 11 | 11400 | 1.20 | 77 | 18 | 15300 | 90 | ~100 | Br |
| 19 | 11800 | 1.19 | 87 | 20 | 14700 | 85 | 90 | Br |

[a]Determined by GPC (THF) using polystyrene standards.
[b]Calculated from integral ratios on NMR spectra.
[c]Conversion of halogenated residues into quaternary amines.

The utility of the organocatalytic system (TU/DBU) was demonstrated through the synthesis of narrowly dispersed homopolymers, random polymers, and block copolymers having predictable molecular weights. The polydispersity ranged from 1.11 to 1.22. The precursor polymers had a number average molecular weight $M_n$ of 10500 to 12400. The cationic polymers had a number average molecular weight $M_n$ of 13100 to 19433. The conversion of halide to quaternary amine was about 84% to 100%.

The reactivity of the precursor polymer with an amine depends on the halide on the side chain. Although the polymer of Example 5 (X=Cl) can form quaternary amine easily with trimethylamine in acetonitrile at room temperature, it needed more polar solvent such as DMSO and heating (90° C.) to produce the cationic polymer of Example 12 with TMEDA (4 equivalents TMEDA per equivalent of [Cl]). In comparison, the precursor polymers of Example 6 (X=Br) and Example 7 (X=I) were converted at room temperature to the corresponding cationic polymers of Example 13 and 14 respectively, using TMEDA in DMSO or acetonitrile. Little difference was found between the reactivity of bromide and iodide in the reaction rate with TMEDA.

The difference in the reactivity between chlorine, bromine and iodine can be helpful in the design of block copolymers, especially amphiphilic block copolymers to form micelles containing the cationic polycarbonate segments. As shown above, a cationic block copolymer can be formed comprising a cationic hydrophilic segment at both ends (Examples 15 to 17) and a hydrophobic core. The hydrophobic core comprises repeat units derived from trimethylene carbonate (TMC) or a lactide (LLA or DLA). However, the hydrophobic core derived from LLA and DLA was found to be thermally labile during TMEDA quaternization reactions that required heat, in particular with polycarbonate subunits bearing a chloride leaving group. Consequently, these monomers were employed to form precursor polymers having bromide or iodide leaving groups, which could react with TMEDA at room temperature. For precursor polymers comprising chloride leaving groups, a hydrophobic block comprising poly(trimethylene carbonate) derived from TMC was relatively stable at the elevated temperature used in the TMEDA quaternization reaction.

The reactivity of halogens may also affect the stability of the charged polymers. Although around 90% of halogen residues are converted, it is difficult to convert all side chain halide groups to quaternary amine, owing to the reaction equilibrium, steric hindrance, and charge repulsion, even when excess TMEDA is used. The unreacted alkyl halide groups are potential crosslinking sites for reaction with the tertiary amine at the very end of the side chain. The cationic polymers derived from chloride-containing precursor polymers are quite stable because of their low reactivity, whereas the cationic polymers derived from bromide or iodide containing precursor polymers included a small amount of insoluble material. However, no crosslinking was observed in the reaction to produce the cationic polymer of Example 18 derived from the random precursor polymer of Example 11. The cationic polymer of Example 18 showed good solubility in water when the comonomer molar ratio MTCO-Et:MTCOPrBr was 1:1.

Physicochemical and Biological Tests.

General Procedure for Preparation of Polymer/DNA and PEI/DNA Complexes.

The polymer was dissolved in ultra pure water (HPLC grade, pH 7.0) or 20 mM sodium acetate buffer (pH 5.0 or 6.0) and PEI was dissolved in ultra pure water. The complexes were formed directly by mixing equal volume of polymer or PEI and DNA solutions to achieve the intended N/P ratios (the ratio of moles of the amine groups of the cationic polymer to those of the phosphate groups of DNA). To allow for complete electrostatic interaction between the polymer or PEI and DNA molecules, the solution was equilibrated at room temperature for 30 minutes upon mixing before being used for further studies.

Gel Retardation Assay.

Various formulations of polymer/DNA complexes were prepared with different N/P ratios. Post-equilibration, the complexes were electrophoresed on 1% agarose gel (stained with 4 microliters of 0.5 microgram/mL ethidium bromide per 50 mL of agarose solution) in 0.5×TBE buffer at 80 mV for 60 minutes. A stock solution of TBE buffer contains 53 g of TRIS base, $(HOCH_2)_3CNH_2$; 27.5 g of boric acid, and 20 ml of 0.5 M ethylenediamine tetraacetic acid (EDTA) (pH 8.0). The TBE stock solution was diluted 0.5× before use. The gel was then analyzed on a UV illuminator (Chemi Genius, Evolve, Singapore) to show the position of the complexed DNA relative to that of the naked DNA.

Particle Size and Zeta Potential Analyses.

The polymer/DNA complexes were prepared according to N/P 1, 5, 10, 20, 30, 40 and 50. After 30 minutes of incubation, 100 microliter of the complex solutions were diluted 11 times with 1 mL of ultra pure water or 20 mM sodium acetate buffer (pH 5.0 or pH 6.0). Naked DNA, diluted to the same concentration with ultra pure water or the sodium acetate buffer, was employed as control. Prior to analysis, the diluted complex solutions were allowed to stabilize for 30 minutes. The particle size of the polymer/DNA complexes were measured using dynamic light scattering (Brookhaven Instrument Corp., Holtsville, N.Y., U.S.A.) equipped with a He—Ne laser beam at 658 nm (scattering angle: 90) and Zetasizer (Malvern Instrument Ltd., Worchestershire, UK), respectively. The particle size and zeta potential measurements were repeated for 5 runs for each sample, and the data were reported as the average of 5 readings.

Cytotoxicity Test.

HepG2 cells were maintained in DMEM growth medium supplemented with 10% FBS (fetal bovine serum), 100 microgram/mL penicillin and 100 units/mL streptomycin at 37° C., under the atmosphere of 5% $CO_2$. To assess the cytotoxicity of polymer/DNA complexes in HepG2 cells, a standard MTT (Dimethyl thiazolyl diphenyl tetrazolium salt) assay protocol was employed. On a 96-well plate, cells were seeded at a density of $1 \times 10^4$ cells/well and allowed to grow for 24 hours to reach 60% to 70% confluence. The DNA complexes were prepared according to the protocol described above. Naked DNA solutions were also prepared to the same concentration as that of the complex solutions. Each well was replaced with 100 microliters of fresh growth medium and treated with 10 microliters of the complex solution. The cytoxicity test was performed in replicates of 8 wells per N/P ratio. After 4 hours of incubation, the wells were replaced with fresh medium and incubated further for 68 hours. Upon replacing the wells with 100 microliters of fresh medium and 20 microliters of MTT solution (5 mg/mL in PBS buffer), the cells were incubated for another 4 hours. Finally, the used media were removed and the internalized purple formazan crystals in each well were dissolved with 150 microliters of DMSO. A 100 microliter aliquot of the formazan/DMSO solution was transferred from each well to a new 96-well plate, and the absorbance (A) was measured using a microplate spectrophotometer (BioTek Instruments Inc, Winooski, Vt., U.S.A.) at the wavelength of 550 nm and 690 nm. To measure the relative cell viability in different N/P ratios, the absorbance of formazan solution in the treated cells were compared to that of the control cells:

$$\text{Cell viability} = [(A_{550} - A_{690})\text{sample}/(A_{550} - A_{690})\text{control}] \times 100\%$$

The data were statistically analyzed for significant differences, based on the Student's t-test at $p < 0.05$.

In Vitro Gene Expression.

The in vitro gene transfection of the polymer/DNA complexes was studied in HepG2 cells. Cells were seeded onto a 24-well plate at a density of $8 \times 10^4$ cells/well and cultivated with 0.5 mL of DMEM (Dulbecco's modi ed Eagle's medium) growth medium for 24 hours until 60% to 70% confluent. The cells in each well were replaced with fresh growth medium, and subsequently transfected with 50 microliters of the complex solution (containing 2.5 micrograms of DNA). After 4 hours of transfection, the used media were replaced with fresh media and the cells were incubated further. The culture media were removed after 68 hours and the cells were washed with PBS buffer (phosphate buffered saline, containing 137 mM NaCl, 2.7 mM KCl, 10 mM podium phosphate dibasic, 2 mM potassium phosphate monobasic, pH of 7.4) before being added with 0.2 mL of 1× reporter lysis buffer. After being subjected to two cycles of freezing (−80° C. for 30 minutes) and thawing, the cell lysates were centrifuged at 14,000 rpm and 4° C. for 10 minutes to remove cell debris. The supernatant (20 microliters) was mixed with 100 microliters of luciferin substrate buffer, and its fluorescence intensity (in terms of relative light units RLU) was immediately measured using a luminometer (Lumat LB9507, Mandel Scientific Inc, Ontario, Canada). The RLU readings were normalized against protein concentration of the supernatant, determined by BCA protein assay, to give the overall expression efficiency.

In all in vitro gene expression experiments, naked DNA was used as negative control. PEI/DNA complexes were used as positive control, and were prepared at the optimal N/P ratio (i.e., 10), at which PEI induced high gene expression yet provided more than 50% cell viability. The luciferase expression efficiency at each N/P ratio was expressed as an average of 6 replicate wells. Statistical analysis was performed using the Student's t-test. Differences were considered statistically significant at $p < 0.05$.

The above prepared amphiphilic polymers (Examples 12 to 18) can form micellar nanoparticles in aqueous solutions. As a typical example, cationic polymer of Example 15 formed nanoparticles with size of 370 nm and zeta potential of 34 mV by direct dissolution of the polymer in 20 mM sodium acetate buffer (pH 6.0). Polyplexes based on the cationic polymer of Example 15 exhibited strong binding ability to DNA. FIG. 1 is a photograph showing the results of agarose gel electrophoresis of polyplexes prepared at different pH and at various N/P ratios using the cationic polymer of Example 15. For polyplexes prepared at pH 7 complete retardation of DNA mobility was observed at N/P=4. For polyplexes prepared at pH 6 or pH 5, complete retardation of DNA mobility was observed at N/P=3. At lower pH more tertiary amines are protonated, enhancing DNA binding ability of the cationic polymer. Moreover, the polyplexes had a particle size less than 150 nm, and a positive zeta potential at high N/P ratios, which are advantageous for cellular uptake.

Figure 2:
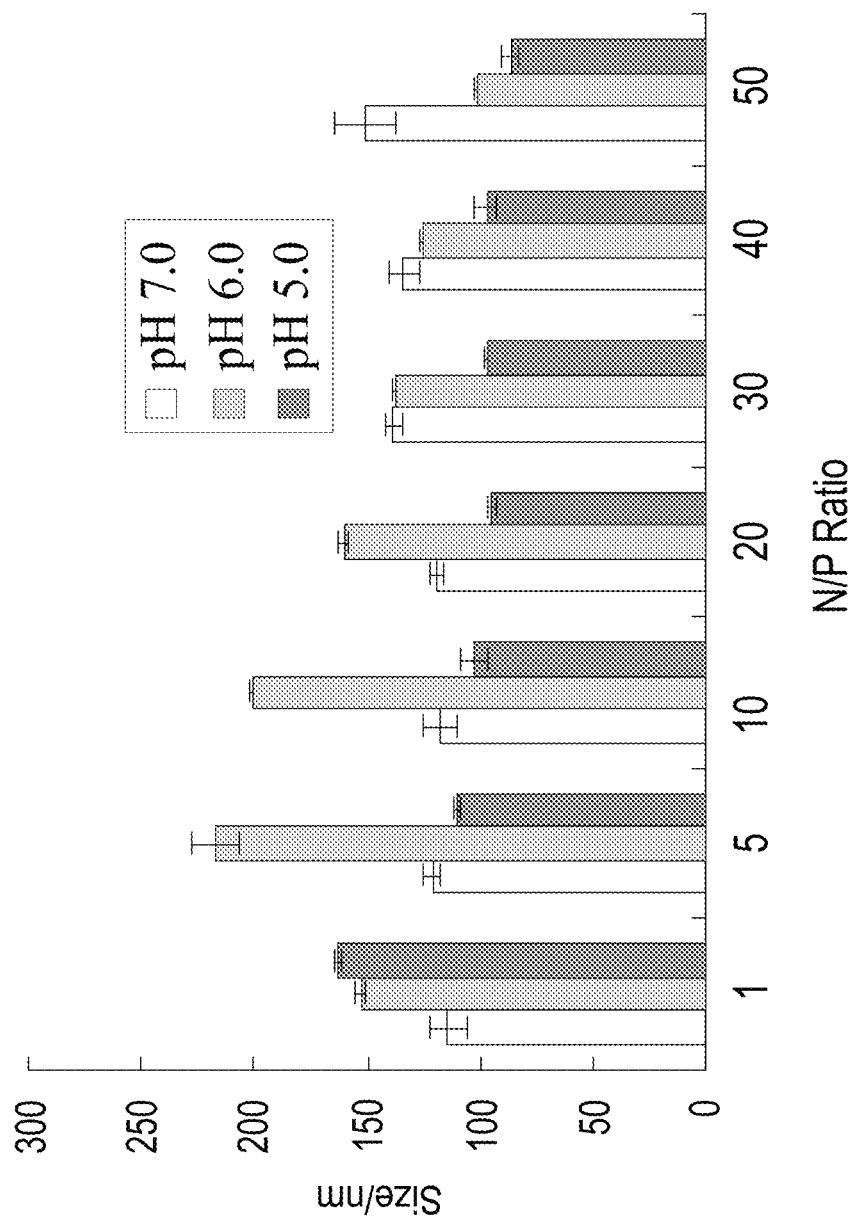
FIG. 2 is a bar chart showing the relationship between N/P ratio and particle size of the polyplex prepared at pH 7.0, 6.0 and 5.0.

FIG. 2 is a bar chart showing the relationship between N/P ratio and particle size of the polyplex prepared at pH 7.0, 6.0 and 5.0. Particle size decreased with increasing N/P ratios (5 to 50) for pH 5.0 (from 110 nm to about 80 nm) and for pH 6.0 (about 250 nm to about 100 nm). For pH 7.0 the particle size remained relatively constant or slightly increased (about 120 nm to 150 nm) for the N/P ratios 1 to 50.

Figure 3:
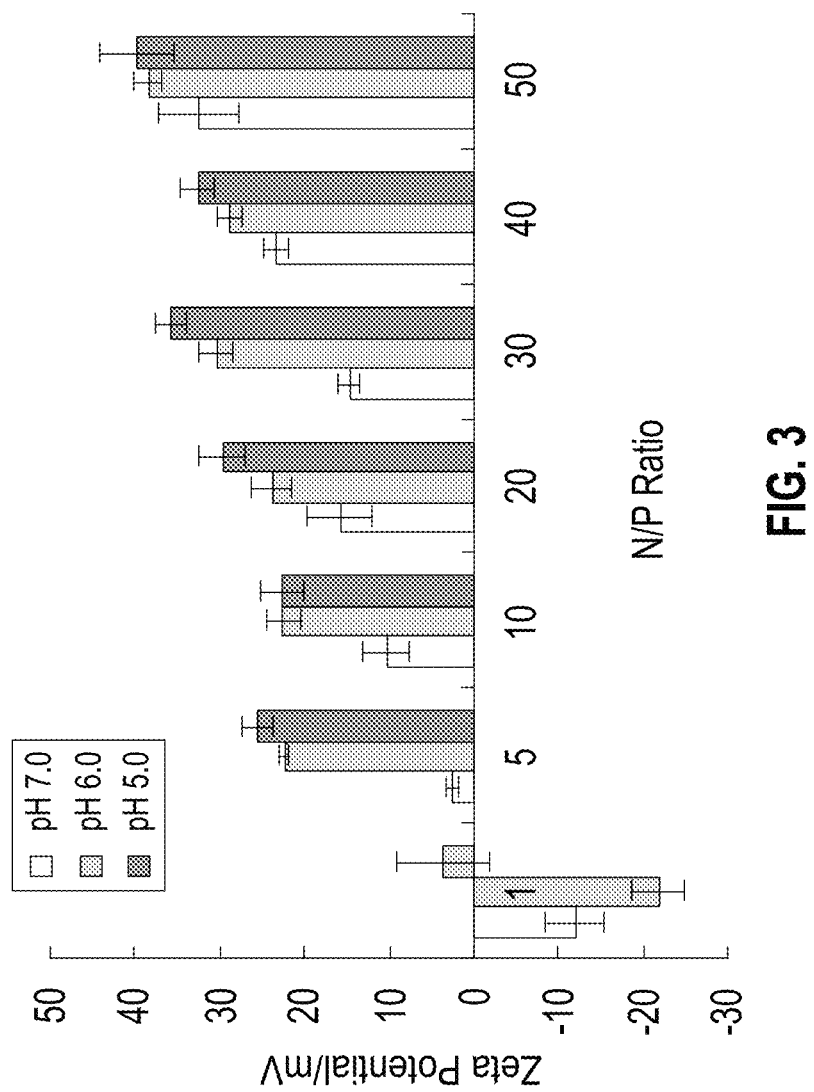
FIG. 3 is a bar chart showing the relationship between N/P ratio and zeta potential of the polyplex prepared at pH 7.0, 6.0 and 5.0.

FIG. 3 is a bar chart showing the relationship between N/P ratio and zeta potential of the polyplex prepared at pH 7.0, 6.0 and 5.0. The zeta potential was highest for high N/P ratios and lower pH values, indicating that the polyplex has higher positive charge density at lower pH, and therefore greater DNA binding capacity.

Figure 4:
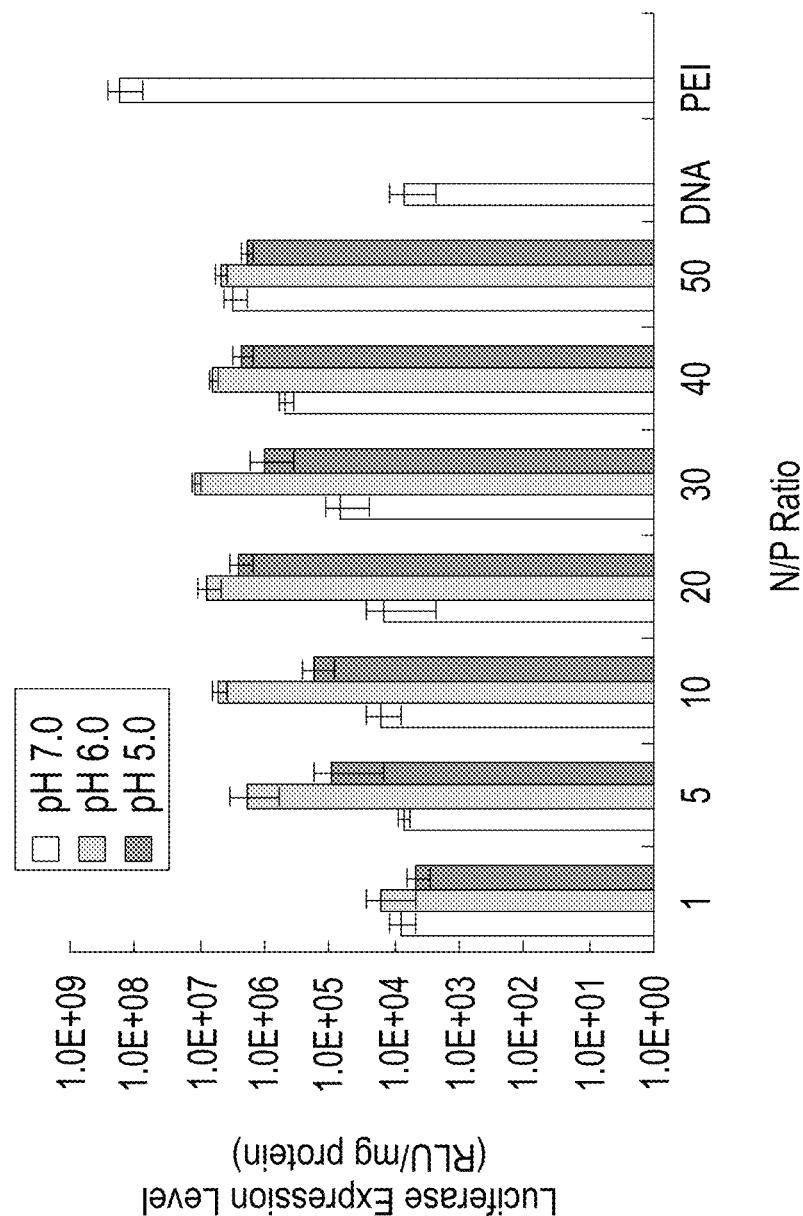
FIG. 4 is a bar chart comparing luciferase expression levels in HepG2 human liver carcinoma cell line for polyplexes fabricated at different pH and N/P ratios. DNA and PEI/DNA controls are also shown.

FIG. 4 is a bar chart comparing luciferase expression levels in HepG2 human liver carcinoma cell line for polyplexes fabricated at different pH and N/P ratios. DNA and PEI/DNA controls are also shown. Among three pH conditions, pH 6.0 yielded the highest gene expression level, which was $1.1 \times 10^7$ RLU/mg protein at N/P 30. As shown in FIGS. 2 and 3, although the polyplexes had similar particle size at high N/P ratios (e.g., 30 to 50) when prepared at pH 7.0 and pH 6.0, the polyplexes fabricated at pH 6.0 had higher zeta potential. Without being bound by theory, the higher zeta potential might enhance the interaction of the polyplexes with negatively charged cell membrane, promoting cellular uptake of the polyplexes and thus increasing gene expression efficiency. The tertiary amines were designed to provide proton sponge effect for endosomal escape of the polyplexes. Compared to pH 6.0, more tertiary amines are protonated at pH 5.0, which might weaken the proton sponge effect and caused the observed lower gene expression levels.

Figure 5:
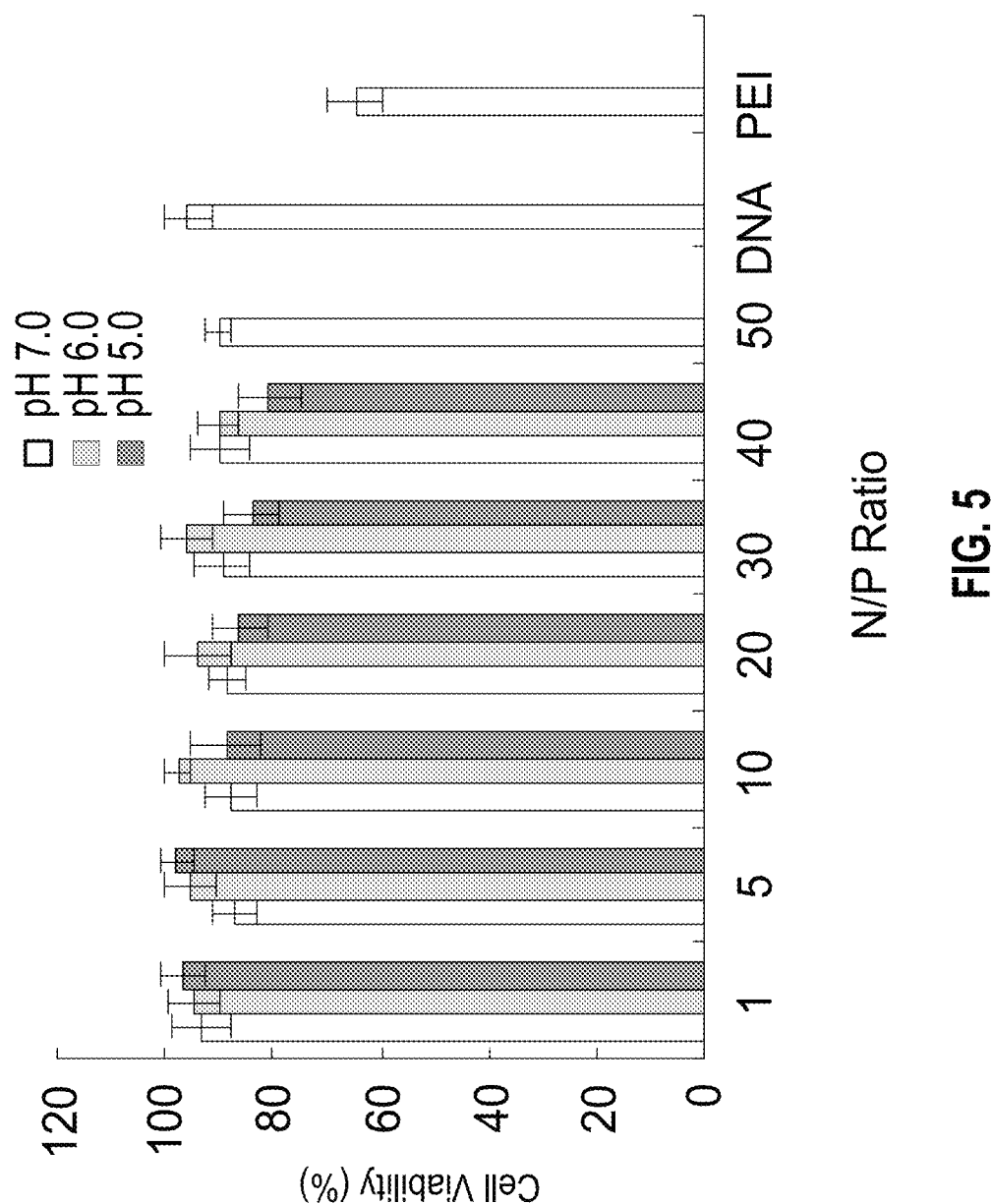
FIG. 5 is a bar chart comparing cell viability at different pH and N/P ratios.

Cell viability data is shown in the bar chart of FIG. 5. Although the highest gene expression level induced by the polyplexes (at pH 6.0 and N/P 30) was lower than that mediated by PEI at its optimal N/P ratio (i.e., N/P 10), the polyplexes had much lower cytotoxicity than the PEI/DNA complexes. For example, the cell viability was 96% for the disclosed polyplexes, but only 64% for PEI/DNA complexes. The improved viability is attributed to the greater biodegradability of the disclosed polymers.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A polymer complex, comprising:
a negatively charged biologically active material selected from the group consisting of genes, nucleotides, proteins, peptides, drugs, and combinations thereof; and
a biodegradable cationic polymer comprising two polymer chains joined by a divalent linking group, wherein each of the polymer chains comprises
i) a first repeat unit selected from the group consisting of:

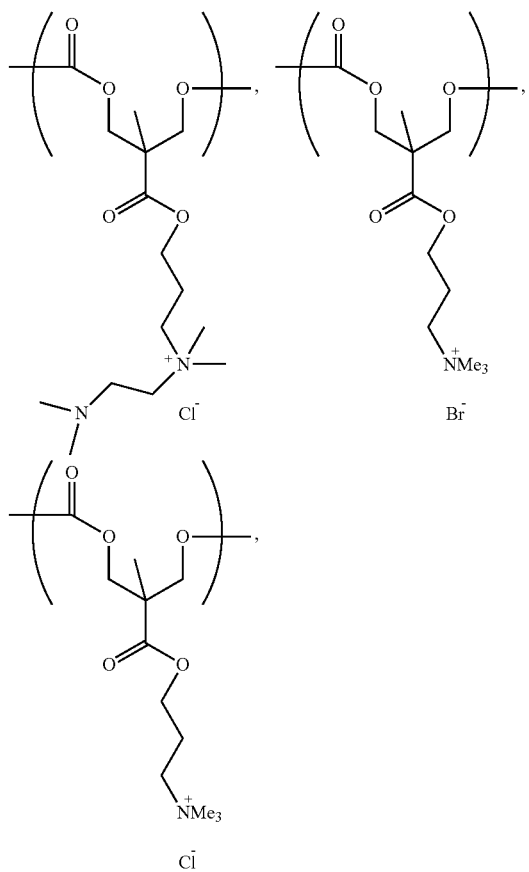

-continued

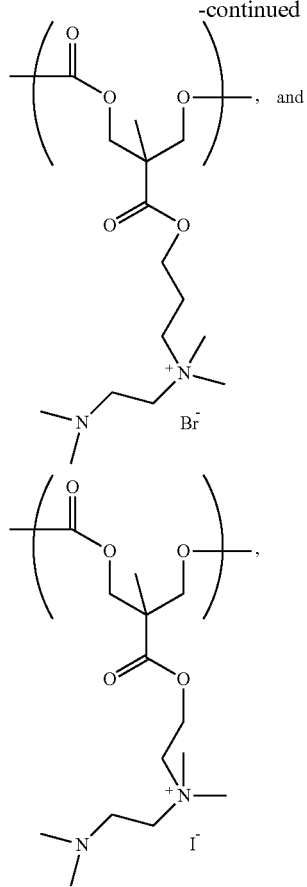

and ii) an optional second repeat unit; wherein the biologically active material and the cationic polymer are bound together by non-covalent interactions, and the polymer complex is capable of entering a cell by endocytosis and releasing the biologically active material within the cell.

2. The polymer complex of claim 1, wherein the first repeat unit is

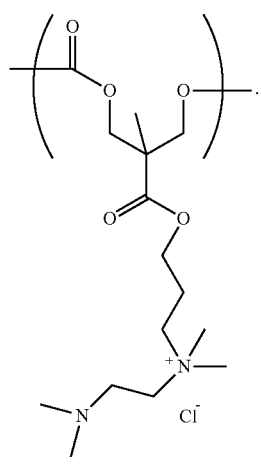

3. The polymer complex of claim 1, wherein the first repeat unit is

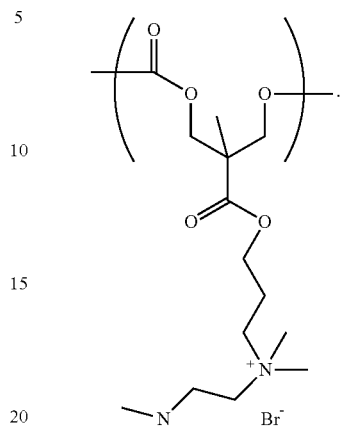

4. The polymer complex of claim 1, wherein the first repeat unit is

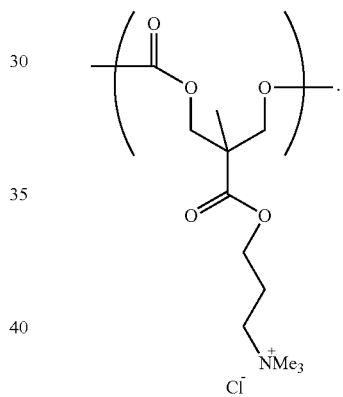

5. The polymer complex of claim 1, wherein each of the polymer chains is a polycarbonate homopolymer of the first repeat unit.

6. The polymer complex of claim 1, wherein each of the polymer chains is a polycarbonate random copolymer of the first repeat unit and the second repeat unit, wherein the second repeat unit is selected from the group consisting of

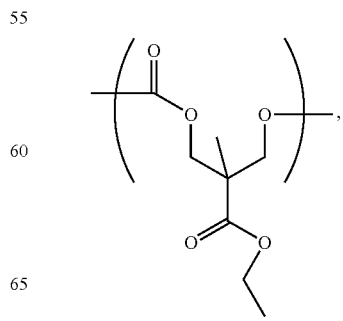

-continued

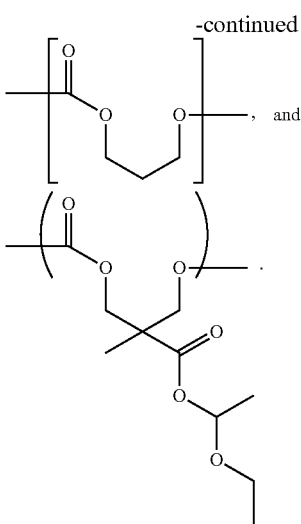

, and

7. The polymer complex of claim 6, wherein the second repeat unit is

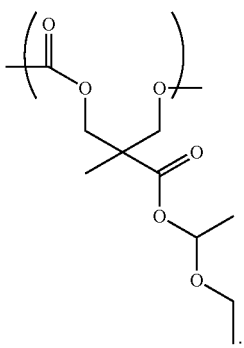

.

8. The polymer complex of claim 1, wherein each of the polymer chains is a diblock copolymer chain comprising i) a hydrophobic core block linked to the divalent linking group of the cationic polymer and ii) a hydrophilic outer block linked to the hydrophobic core block, the hydrophilic outer block comprising the first repeat unit.

9. The polymer complex of claim 8, wherein the hydrophobic core block is a polycarbonate.

10. The polymer complex of claim 9, wherein the hydrophobic core block is a poly(trimethylene carbonate).

11. The polymer complex of claim 8, wherein the hydrophobic core block is a polyester.

12. The polymer complex of claim 11, wherein the hydrophobic core block is poly(L-lactide).

13. The polymer complex of claim 11, wherein the hydrophobic core block is poly(D-lactide).

14. The polymer complex of claim 1, wherein the cationic polymer self-assembles in water to form nanoparticles having an average particle size of 10 nm to 500 nm at a pH of from 5.0 to 8.0.

15. The polymer complex of claim 14, wherein in water the nanoparticles of the cationic polymer have a positively charged surface and a hydrophobic core.

16. The polymer complex of claim 1, wherein the polymer complex in water has an average particle size of 50 nm to 500 nm at a pH of from 5.0 to 8.0.

17. The polymer complex of claim 1, wherein the biologically active material is a gene.

18. The polymer complex of claim 1, wherein the biologically active material is a drug.

19. The polymer complex of claim 1, wherein the cationic polymer is biodegradable in accordance with ASTM D6400.

20. A method of treating a cell, comprising:
contacting the cell with nanoparticles of the polymer complex of claim 1 in water , wherein the polymer complex enters the cell, the polymer complex releases the biologically active material within the cell, and the released biologically active material alters a chemical structure and/or activity of the cell.

21. The method of claim 20, wherein the nanoparticles have an average particle size of 50 nm to 500 nm at a pH of from 5.0 to 8.0.

22. The method of claim 20, wherein the cell is a eukaryotic cell.

23. The method of claim 22, wherein the biologically active material is a gene, the polymer complex releases the gene within the cell, and the gene is incorporated into deoxyribonucleic acid (DNA) of the cell.

24. The method of claim 23, wherein the cell expresses the gene.

25. The method of claim 20, wherein the biologically active material is a drug.

* * * * *